(12) United States Patent
Ochiya et al.

(10) Patent No.: US 10,961,507 B2
(45) Date of Patent: Mar. 30, 2021

(54) METHOD FOR PRODUCING HEPATIC STEM/PRECURSOR CELLS FROM MATURE HEPATIC CELLS USING LOW-MOLECULAR-WEIGHT COMPOUND

(71) Applicant: Cynity Co., Ltd., Tokyo (JP)

(72) Inventors: Takahiro Ochiya, Tokyo (JP); Takeshi Katsuda, Tokyo (JP)

(73) Assignee: Cynity Co., Ltd., Tokyo (JP)

( * ) Notice: Subject to any disclaimer, the term of this patent is extended or adjusted under 35 U.S.C. 154(b) by 3 days.

(21) Appl. No.: 16/068,607

(22) PCT Filed: Jan. 6, 2017

(86) PCT No.: PCT/JP2017/000342
§ 371 (c)(1),
(2) Date: Jul. 6, 2018

(87) PCT Pub. No.: WO2017/119512
PCT Pub. Date: Jul. 13, 2017

(65) Prior Publication Data
US 2019/0010464 A1 Jan. 10, 2019

(30) Foreign Application Priority Data
Jan. 8, 2016 (JP) .............................. JP2016-003088

(51) Int. Cl.
| | | |
|---|---|---|
| *C12N 5/071* | (2010.01) | |
| *A61K 35/407* | (2015.01) | |
| *C12Q 1/02* | (2006.01) | |
| *A61P 1/16* | (2006.01) | |
| *G01N 33/50* | (2006.01) | |

(52) U.S. Cl.
CPC .......... *C12N 5/0672* (2013.01); *A61K 35/407* (2013.01); *A61P 1/16* (2018.01); *C12Q 1/02* (2013.01); *G01N 33/5014* (2013.01); *G01N 33/5067* (2013.01); *C12N 2501/15* (2013.01); *C12N 2501/727* (2013.01)

(58) Field of Classification Search
None
See application file for complete search history.

(56) References Cited

U.S. PATENT DOCUMENTS

| | | |
|---|---|---|
| 2012/0021519 A1 | 1/2012 | Ichida et al. |
| 2012/0264218 A1 | 10/2012 | Lin et al. |
| 2013/0071931 A1 | 3/2013 | Ishikawa |
| 2016/0206664 A1 | 7/2016 | Sokal et al. |

FOREIGN PATENT DOCUMENTS

| | | |
|---|---|---|
| EP | 2 532 741 A1 | 12/2012 |
| JP | 2013-507932 | 7/2013 |
| WO | WO 2010/033906 A2 | 3/2010 |
| WO | WO 2013/018851 A1 | 2/2013 |
| WO | WO 2014/058080 A1 | 4/2014 |
| WO | WO 2015/028577 A1 | 3/2015 |

OTHER PUBLICATIONS

Sampaziotis, Fotios, et al. "Cholangiocytes derived from human induced pluripotent stem cells for disease modeling and drug validation." Nature biotechnology 33.8 (2015): 845. (Year: 2015).*
Liu, Hua, et al. "Generation of endoderm-derived human induced pluripotent stem cells from primary hepatocytes." Hepatology 51.5 (2010): 1810-1819. (Year: 2010).*
Tomizawa, Minoru, et al. "Single-step protocol for the differentiation of human-induced pluripotent stem cells into hepatic progenitor-like cells." Biomedical reports 1.1 (2013): 18-22. (Year: 2013).*
International Preliminary Report on Patentability for related application International Application No. PCT/JP2017/000342, dated Jun. 13, 2018, 15 pages (with translation).
International Search Report for related application International Application No. PCT/JP2017/000342, dated Jul. 13, 2017, 4 pages.
Katsuda et al., "Conversion of Terminally Committed Hepatocytes to Culturable Bipotent Progenitor Cells with Regenerative Capacity", Cell Stem Cell vol. 20, Jan. 5, 2017, pp. 41-55.
Katsuda et al., "Reprogramming of rat mature hepatocytes to bipotent hepatic stem cells", 21st Annual Meeting of the Japanese Society for the Research of Hepatic Cells, pp. 42-43, Nov. 12, 2014 (original in Japanese, with translation).
Tarlow et al., "Bipotential adult liver progenitors are derived from chronically injured mature hepatocytes", Cell Stem Cell, Nov. 6, 2014, vol. 15(5), pp. 605-618.
Miyajima et al., "Stem/Progenitor Cells in Liver Development, Homeostasis, Regeneration, and Reprogramming", Author Manuscript. Cell Stem Cell 14, May 1, 2014, pp. 561-574.
Hou et al., "Pluripotent Stem Cells Induced from Mouse Somatic Cells by Small-Molecule Compounds", Science, vol. 341, Aug. 9, 2013, pp. 651-654.
Zhu et al., "Mouse liver repopulation with hepatocytes generated from human fibroblasts", Nature, vol. 508, Apr. 3, 2014, pp. 93-97, with Online Methods and Extended Data (13 pp).
Yanger et al., "Robust cellular reprogramming occurs spontaneously during liver regeneration", Genes & Development, 27:719-724, 2013, pp. 719-724, with Erratum notice (1p).
Huang et al., "Induction of functional hepatocyte-like cells from mouse fibroblasts by defined factors", Nature, vol. 475, Jul. 21, 2011, pp. 386-389, with Online Methods (1p).
Sekiya and Suzuki, "Direct conversion of mouse fibroblasts to hepatocyte-like cells by defined factors", Nature, vol. 475, Jul. 21, 2011, pp. 390-393, with Online Methods (3pp).
Kawamata and Ochiwa, "Generation of genetically modified rats from embryonic stem cells", Proc. Nat. Acad. Sci., vol. 107, No. 32, Aug. 10, 2010, pp. 14223-14228.

(Continued)

*Primary Examiner* — Robert J Yamasaki
(74) *Attorney, Agent, or Firm* — Fish & Richardson P.C.

(57) ABSTRACT

The present invention provides a method for producing hepatic stem/progenitor cells from mammal hepatocytes, comprising bringing a TGFβ-receptor inhibitor, and optionally a GSK3 inhibitor and/or a ROCK inhibitor into contact with the hepatocytes in vitro.

3 Claims, 11 Drawing Sheets

(56) References Cited

OTHER PUBLICATIONS

Extended European Search Report for related application EP Application No. 17736049.2, dated Aug. 16, 2019, 12 pages.
Lv et al., "Self-Renewal of Hepatoblasts Under Chemically Defined Conditions by Iterative Growth Factor and Chemical Screening", Hepatology, vol. 61, No. 1, pp. 337-347 (2014).
Chen et al., "Mature Hepatocytes Exhibit Unexpected Plasticity by Direct Dedifferentiation into Liver Progenitor Cells in Culture", Hepatology, vol. 55, No. 2, pp. 563-574 (2012).
Dorrell et al., "Prospective Isolation of a Bipotential Clonogenic Liver Progenitor Cell in Adult Mice", Genes and Development, vol. 25, No. 11, pp. 1193-1203 (2011).
Tanaka et al., "Liver Stem/Progenitor Cells: Their Characteristics and Regulatory Mechanisms". Journal of Biochemistry, vol. 149, No. 3, pp. 231-239 (2011).

\* cited by examiner

METHOD FOR PRODUCING HEPATIC STEM/PRECURSOR CELLS FROM MATURE HEPATIC CELLS USING LOW-MOLECULAR-WEIGHT COMPOUND

CLAIM OF PRIORITY

This application is a 371 U.S. National Phase Application of PCT/JP2017/000342, filed on Jan. 6, 2017, which claims the benefit of Japanese Patent Application Serial No. 2016-003088, filed on Jan. 8, 2016. The entire contents of the foregoing are hereby incorporated by reference.

TECHNICAL FIELD

The present invention relates to a method for producing hepatic stem/progenitor cells from mature hepatocytes using a low-molecular-weight compound, to an agent for inducing hepatic stem/progenitor cells from mature hepatocytes comprising said low-molecular-weight compound, and the like.

BACKGROUND ART

Although advances in stem cell biology have aroused great interest in its applications in liver regenerative medicine, they have not yet been realized. Although induced pluripotent stem cells (iPS cells), one of the most promising cell sources, have been studied intensively, their applications are still limited due to difficulty in efficient differentiation into functional hepatocytes, and the remaining presence of tumorigenesis risk. Even a recently developed method is incapable of generating hepatocytes with the ability to regenerate an injured liver as efficient as mature hepatocytes (Non-patent document 1). Meanwhile, recent study has shown that cells of different lineage can directly be converted (directly reprogrammed) into hepatocyte-like cells (Non-patent documents 2 and 3). In spite of such a promising finding, direct reprogramming is still associated with unexpected risks since it involves genetic modification like iPS cells, and thus cannot be applied to regenerative medicine.

Recently, several groups reported surprising findings that adult hepatocytes are reprogrammed into proliferative, bipotential hepatic stem/progenitor cells when a liver is chronically injured (Non-patent documents 4 and 5). These innovative findings provide great insight not only to the hepatic stem cell theory but also to the liver regeneration studies. Specifically, if such reprogramming can be reproduced in vitro, the resulting hepatic stem/progenitor cells are expected to serve as a new cell source in liver regenerative medicine.

However, a method for reprogramming mature hepatocytes into hepatic stem/progenitor cells without genetic modification is totally unknown.

The present inventors and other groups have previously reported that a combination of certain types of low-molecular weight inhibitors contributes to the induction and maintenance of pluripotency of stem cells (Non-patent documents 6 and 7). However, there is no report about contribution of these low-molecular weight inhibitors to the reprogramming of mature hepatocytes into hepatic stem/progenitor cells at all.

PRIOR ART DOCUMENTS

Non-Patent Documents

Non-patent document 1: Zhu, S. et al., Nature 508, 93-97 (2014)
Non-patent document 2: Huang, P. et al., Nature 475, 386-389 (2011)
Non-patent document 3: Sekiya, S., and Suzuki, A. Nature 475, 390-393 (2011)
Non-patent document 4: Tarlow, B. D. et al., Cell Stem Cell 15, 605-618 (2014)
Non-patent document 5: Yanger, K. et al., Genes Dev. 27, 719-724 (2013)
Non-patent document 6: Hou, P. et al., Science 341, 651-654 (2013)
Non-patent document 7: Kawamata, M. and Ochiya, T. Proc. Natl. Acad. Sci. USA, 107,14223-14228 (2010)

SUMMARY OF INVENTION

Problem to be Solved by Invention

The objective of the present invention is to provide a method for efficiently reprogramming mature hepatocytes into hepatic stem/progenitor cells without genetic modification.

Means for Solving Problem

In order to achieve the above-described objective, the present inventors have gone through intensive research, and as a result of which found that mature hepatocytes of a mammal can be cultured in the presence of a TGFβ-receptor inhibitor so that said cells can be reprogrammed into proliferative, bipotential cells that can differentiate into both hepatocytes and biliary epithelial cells. Furthermore, they succeeded in improving the reprogramming efficiency by combining a TGFβ-receptor inhibitor with a glycogen synthase kinase-3 (GSK3) inhibitor or a Rho kinase (ROCK) inhibitor. The effect in improving the reprogramming efficiency was more significant when a TGFβ-receptor inhibitor was combined with a GSK3 inhibitor. When three of a TGFβ-receptor inhibitor, a GSK3 inhibitor and a ROCK inhibitor were combined, the difference in the reprogramming efficiency was little from the combination of a TGFβ-receptor inhibitor and a GSK3 inhibitor but combinational use of the three agents was found to give greater cell proliferation ability. When the thus-obtained mature hepatocyte-derived hepatic stem/progenitor cells were transplanted into an immunodeficient mouse with chronic liver damage, they showed liver regeneration ability comparative to that obtained with mature hepatocytes.

As a result of further studies based on these findings, the present inventors accomplished the present invention.

Thus, the present invention is as follows.

(1) A method for producing hepatic stem/progenitor cells from mammal hepatocytes, comprising bringing a TGFβ-receptor inhibitor into contact with the hepatocytes in vitro.

(2) The method according to (1), further comprising bringing a GSK3 inhibitor and/or a ROCK inhibitor into contact with the hepatocytes in vitro.

(3) The method according to (1), further comprising bringing a GSK3 inhibitor and a ROCK inhibitor into contact with the hepatocytes in vitro.

(4) The method according to any one of (1)-(3), wherein the contact between the hepatocytes and the TGFβ-receptor inhibitor is carried out by culturing the hepatocytes in the presence of the inhibitor.

(5) The method according to any one of (2)-(4), wherein the contact between the hepatocytes and the GSK3 inhibitor and/or the ROCK inhibitor is carried out by culturing the hepatocytes in the presence of the inhibitor.

(6) The method according to any one of (1)-(5), wherein the mammal is a human, a rat or a mouse.

(7) An agent for inducing hepatic stem/progenitor cells from hepatocytes, which comprises a TGFβ-receptor inhibitor.

(8) The agent according to (7), which is combined with a GSK3 inhibitor and/or a ROCK inhibitor.

(9) The agent according to (7), which is combined with a GSK3 inhibitor and a ROCK inhibitor.

(10) The agent according to any one of (7)-(9), wherein the hepatocytes are derived from a human, a rat or a mouse.

(11) Hepatic stem/progenitor cells derived from mammal hepatocytes, comprising the following characteristics:
(a) have self-regeneration ability;
(b) capable of differentiating into both hepatocytes and biliary epithelial cells; and
(c) express EpCAM but not Dlk1 as a surface antigen marker.

(12) The agent according to any one of (7)-(10), which is used as an agent for maintaining/proliferating the hepatic stem/progenitor cells obtained by the method according to any one of (1)-(6) or the hepatic stem/progenitor cells according to (11).

(13) A method for maintaining/proliferating the hepatic stem/progenitor cells obtained by the method according to any one of (1)-(6) or the hepatic stem/progenitor cells according to (11), the method comprising passaging the hepatic stem/progenitor cells in the presence of a TGFβ-receptor inhibitor, a GSK3 inhibitor and a ROCK inhibitor:
(i) on a collagen- or Matrigel-coated culture vessel for the first to fourth passages; and
(ii) on a Matrigel-coated culture vessel for the fifth passage and so forth.

(14) A method for inducing biliary epithelial cells from the hepatic stem/progenitor cells obtained by the method according to any one of (1)-(6) and (13) or the hepatic stem/progenitor cells according to (11), the method comprising the steps of:
(i) culturing the hepatic stem/progenitor cells on feeder cells at low density in the presence of a TGFβ-receptor inhibitor, a GSK3 inhibitor and a ROCK inhibitor; and
(ii) further culturing the cells obtained in step (i) in a medium containing Matrigel.

(15) A method for assessing metabolism of a test compound in a mammal body, comprising the steps of:
(i) bringing the test compound into contact with hepatocytes resulting from inductive differentiation of the hepatic stem/progenitor cells obtained by the method according to any one of (1)-(6) and (13) or the hepatic stem/progenitor cells according to (11); and
(ii) measuring metabolism of the test compound in the hepatocytes.

(16) A method for assessing hepatotoxicity of a test compound on a mammal, comprising the steps of:
(i) bringing the test compound into contact with hepatocytes resulting from inductive differentiation of the hepatic stem/progenitor cells obtained by the method according to any one of (1)-(6) and (13), or the hepatic stem/progenitor cells according to (11); and
(ii) measuring the presence or the absence, or the degree of damage in the hepatocytes.

(17) An agent for ameliorating liver damage, comprising the hepatic stem/progenitor cells obtained by the method according to any one of (1)-(6) and (13), or the hepatic stem/progenitor cells according to (11).

(18) A method for ameliorating liver damage in a mammal, comprising administering an effective amount of the hepatic stem/progenitor cells obtained by the method according to any one of (1)-(6) and (13), or the hepatic stem/progenitor cells according to (11) to a mammal with liver damage.

(19) The hepatic stem/progenitor cells obtained by the method according to any one of (1)-(6) and (13), or the hepatic stem/progenitor cells according to (11), for use as an agent for ameliorating liver damage.

Effect of Invention

According to the present invention, hepatic stem/progenitor cells having self-renewal ability and differentiation potency (bipotency) into hepatocytes and biliary epithelial cells can safely and rapidly be induced from hepatocytes without genetic modification.

MODES FOR CARRYING OUT INVENTION

Figure 1:
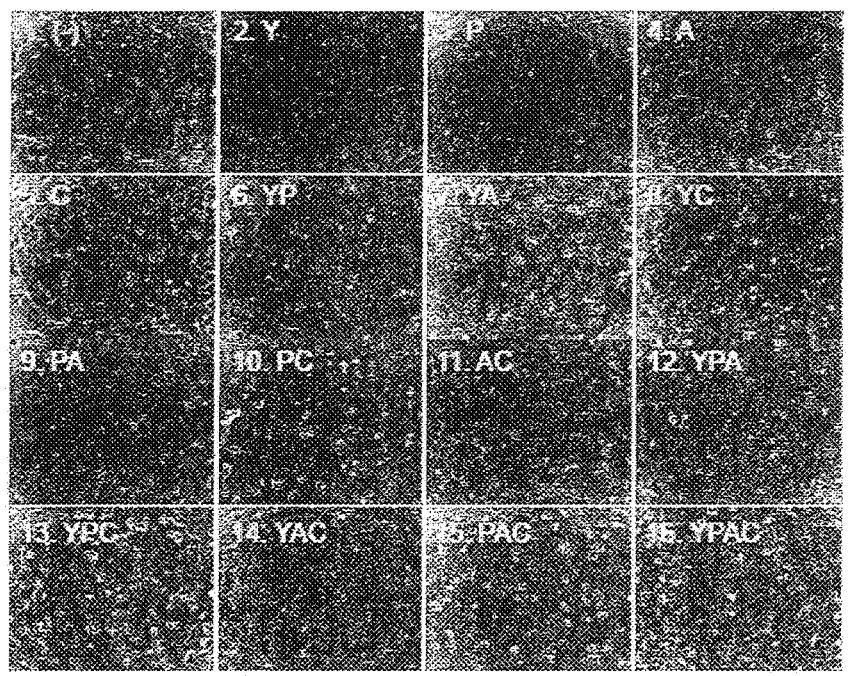
FIG. 1 Views showing the effects of various combinations of a TGFβ-receptor inhibitor (A), a GSK3 inhibitor (C), a ROCK inhibitor (Y) and a MEK inhibitor (P) on reprogramming of primary rat mature hepatocytes into hepatic stem/progenitor cells.
Figure 1:
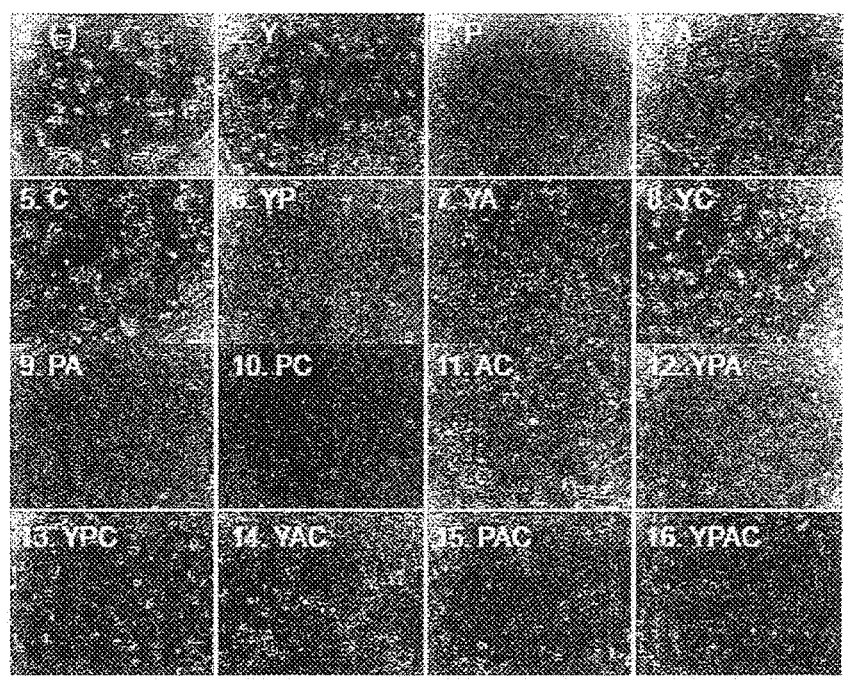

1. Induction of Hepatic Stem/Progenitor Cells from Mature Hepatocytes

The present invention provides a method for producing hepatic stem/progenitor cells from mature hepatocytes (also referred to as a "reprogramming method of the present invention"), comprising brining mammal hepatocytes into contact with one or more low-molecular weight signaling pathway inhibitors comprising at least a TGFβ-receptor inhibitor in vitro.

The "hepatocytes" used as a starting material for the reprogramming method of the present invention refer to cells expressing at least one type of hepatocyte marker genes (for example, albumin (ALB), transthyretin (TTR), glucose-6-phosphatase (G6PC), tyrosine aminotransferase (TAT), tryptophane-2,3-dioxygenase (TDO2), cytochrome P450 (CYP), miR-122, etc.) (preferably 2 or more types, more preferably 3 or more types, still more preferably 4 or more types, particularly preferably 5 or more types, and most preferably all of the 6 types selected from ALB, TTR, G6PC, TAT, TDO2 and CYP). Preferably, the hepatocytes are functional. "Functional" hepatocytes refers to hepatocytes that retain one or more, preferably 2 or more, more preferably 3 or more, still more preferably 4 or more, and most preferably all of the functions selected from: (i) having a bile canalicular structure and accumulating drug metabolites in the canaliculi; (ii) expressing ABC transporters (e.g., MDR1, MRP, etc.) in the cell membrane; (iii) secretorily expressing ALB; (iv) accumulating glycogen; and (v) having activity as a drug-metabolizing enzyme (e.g., CYP1A1, CYP1A2, etc.).

The hepatocytes used for the reprogramming method of the present invention can be provided from any source as long as they are characterized by the expression of the above-described hepatocyte marker genes. For example, they may comprise hepatocytes obtained from mammal (for example, human, rat, mouse, guinea pig, rabbit, sheep, horse, pig, bovine, monkey or the like, preferably human, rat or mouse) embryonic stem cells (ES cells) or pluripotent stem cells such as iPS cells by a differentiation inducing method known per se (for example, Non-patent document 1 mentioned above), or hepatocytes induced from fibroblasts by direct reprogramming (Non-patent documents 2 and 3 mentioned above). However, considering that the main problem of the present invention is to safely and rapidly provide hepatic stem/progenitor cells without genetic modification, hepatocytes isolated/purified from a liver removed from a mammal are favorably used. For example, in a case of a rat, a liver removed from a 10-20-week-old adult rat is preferably used, although a liver derived from a juvenile rat less than 2-month-old may also be used. In a case of a human, an adult liver tissue piece sectioned by surgical operation is preferably used, although a liver sectioned from an aborted fetus may also be used. Alternatively, cells obtained by cryopreserving these isolated/purified hepatocytes removed from the livers (cryopreserved hepatocytes) may also be used.

A method for purifying hepatocytes from a mammal liver or a tissue piece thereof may be a perfusion method ("Handbook of Cultured Cell Experiments" (Yodosha, 2004), etc.). Specifically, following pre-perfusion with an EGTA solution via the portal vein, a liver can be digested by perfusion with an enzyme solution (Hank's solution, etc.) such as collagenase or dispase, the hepatocytes can be purified by removing cell pieces and non-parenchymal cells by filtration, low-speed centrifugation or the like.

The hepatocytes prepared as described above are brought into contact with one or more low-molecular weight signaling pathway inhibitors including a TGFβ-receptor inhibitor in vitro.

The TGFβ-receptor inhibitor used for the present invention may be any inhibitor as long as it inhibits the function of the transforming growth factor (TGF)β-receptor, where examples include 2-(5-benzo [1,3]dioxole-4-yl-2-tert-butyl-1H-imidazol-4-yl)-6-methylpyridine, 3-(6-methylpyridine-2-yl)-4-(4-quinolyl)-1-phenylthiocarbamoyl-1H-pyrazole (A-83-01), 2-(5-chloro-2-fluorophenyl)pteridine-4-yl)pyridine-4-ylamine (SD-208), 3-(pyridine-2-yl)-4-(4-quinonyl)]-1H-pyrazole, 2-(3-(6-methylpyridine-2-yl)-1H-pyrazole-4-yl)-1,5-naphthyridine (all from Merck) and SB431542 (Sigma Aldrich). A preferable example includes A-83-01. The TGFβ-receptor inhibitor also comprises a TGFβ-receptor antagonist.

The TGFβ-receptor inhibitor may be one type of compound or a combination of two or more types compounds.

Examples of a low-molecular weight signaling pathway inhibitor other than the TGFβ-receptor inhibitor preferably include a GSK3 inhibitor and a ROCK inhibitor.

The GSK3 inhibitor used for the present invention may be any inhibitor as long as it inhibits the function of glycogen synthase kinase (GSK)3, where examples include SB216763 (Selleck), CHIR98014, CHIR99021 (all from Axon medchem), SB415286 (Tocris Bioscience), and Kenpaullone (Cosmo Bio). A preferable example includes CHIR99021.

The GSK3 inhibitor may be one type of compound or a combination of two or more types compounds.

The ROCK inhibitor used for the present invention may be any inhibitor as long as it inhibits the function of Rho-binding kinase. Examples of the ROCK inhibitor include GSK269962A (Axon medchem), Fasudil hydrochloride (Tocris Bioscience), Y-27632 and H-1152 (all from, Wako Pure Chemical). A preferable example includes Y-27632.

The ROCK inhibitor may be one type of compound or a combination of two or more types compounds.

As will be described in the examples below, the GSK3 inhibitor and the ROCK inhibitor hardly induce hepatic stem/progenitor cells when they are individually brought into contact with hepatocytes, whereas efficiency of inducing hepatic stem/progenitor cells (also referred to as "reprogramming efficiency") is significantly increased when the GSK3 inhibitor together with the TGFβ-receptor inhibitor are brought into contact with the hepatocytes as compared to the case where only the TGFβ-receptor inhibitor is brought into contact with the hepatocytes. In addition, reprogramming efficiency is also increased when the ROCK inhibitor together with the TGFβ-receptor inhibitor are brought into contact with the hepatocytes as compared to a case where only the TGFβ-receptor inhibitor is brought into contact with the hepatocytes. Therefore, according to the reprogramming method of the present invention, the GSK3 inhibitor and/or the ROCK inhibitor, in addition to the TGFβ-receptor inhibitor, is preferably brought into contact with the hepatocytes. In particular, it is preferable to use: A-83-01 (A) as the TGFβ-receptor inhibitor in combination with CHIR99021 (C) as the GSK3 inhibitor (AC); A-83-01 (A) as the TGFβ-receptor inhibitor in combination with Y-27632 (Y) as the ROCK inhibitor (YA); and A-83-01 (A) as the TGFβ-receptor inhibitor in combination with CHIR99021 (C) as the GSK3 inhibitor and Y-27632 (Y) as the ROCK inhibitor (YAC).

When the GSK3 inhibitor and the ROCK inhibitor are used in combination with the TGFβ-receptor inhibitor, the difference in the reprogramming effect is small from that obtained with a combination of the TGFβ-receptor inhibitor and the GSK3 inhibitor, but the former gives better proliferation ability of the resulting hepatic stem/progenitor cells than the latter. Therefore, in a particularly preferable embodiment of the present invention, the TGFβ-receptor inhibitor, the GSK3 inhibitor and the ROCK inhibitor are brought into contact with the hepatocytes.

According to the reprogramming method of the present invention, a low-molecular weight signaling pathway inhibitor other than the GSK3 inhibitor and the ROCK inhibitor may also be combined with the TGFβ-receptor inhibitor. An example of such an inhibitor includes, but not limited to, a MEK inhibitor. The MEK inhibitor is not particularly limited and any inhibitor may be used as long as it inhibits the function of MEK (MAP kinase-ERK kinase), where examples include AZD6244, CI-1040 (PD184352), PD0325901, RDEA119 (BAY869766), SL327, U0126 (all from Selleck), PD98059, U0124 and U0125 (all from Cosmo Bio).

According to the reprogramming method of the present invention, contact between hepatocytes and the low-molecular weight signaling pathway inhibitors including the TGFβ-receptor inhibitor can be carried out by culturing the hepatocytes in the presence of these inhibitors. Specifically, these inhibitors are added to a medium at an effective concentration to carry out the culturing. As this medium, a medium widely used for culturing animal cells may be utilized as a basal medium. A commercially available basal medium may also be employed, where examples include, but not particularly limited to, a minimum essential medium (MEM), a Dulbecco's modified minimum essential medium (DMEM), a RPMI1640 medium, a 199 medium, a Ham's F12 medium and a William's E medium, which may be used alone or two or more types of them may be used in combination. Examples of additives to the medium include various amino acids (for example, L-glutamine, L-proline, etc.), various inorganic salts (salt of selenious acid, $NaHCO_3$, etc.), various vitamins (nicotinamide, ascorbic acid derivative, etc.), various antibiotics (for example, penicillin, streptomycin, etc.), an antimycotic agent (for example, amphotericin, etc.), and buffers (HEPES, etc.).

In addition, a 5-20% serum (FBS, etc.) may be added to the medium, or the medium may be a serum-free medium. In a case of a serum-free medium, a serum substitute (BSA, HAS, KSR, etc.) may be added. In general, a factor such as a growth factor, cytokine or hormone is further added. Examples of such factors include, but not limited to, epidermal growth factor (EGF), insulin, transferrin, hepatocyte growth factor (HGF), oncostatin M (OsM), hydrocortisone 21-hemisuccinate or a salt thereof and dexamethasone (Dex).

The concentration of the TGFβ-receptor inhibitor added to the medium may suitably be selected, for example, in a range of 0.01-10 µM, and preferably 0.1-1 µM.

The concentration of the GSK3 inhibitor added to the medium may suitably be selected, for example, in a range of 0.01-100 µM, and preferably 1-10 µM.

The concentration of the ROCK inhibitor added to the medium may suitably be selected, for example, in a range of 0.0001-500 µM, and preferably 1-50 µM.

When these inhibitors are water-insoluble or poorly water-soluble compounds, they may be dissolved in a small amount of a low-toxicity organic solvent (for example, DMSO, etc.), and then the resultant can be added to a medium to give the above-described final concentration.

The culture vessel used for this culture is not particularly limited as long as it is suitable for adhesion culture, where examples include a dish, a petri dish, a tissue culture dish, a multidish, a microplate, a microwell plate, a multiplate, a multiwell plate, a chamber slide, a Schale, a tube, a tray, and a culture bag. The culture vessel used may have its inner surface coated with a cell supporting substrate for the purpose of enhancing adhesiveness with the cells. Examples of such a cell supporting substrate include collagen, gelatin, Matrigel, poly-L-lysine, laminin and fibronectin, and preferably collagen and Matrigel.

The hepatocytes can be seeded onto a culture vessel at a cell density of $10^2$-$10^6$ cells/cm$^2$, and preferably $10^3$-$10^5$ cells/cm$^2$. Culture can take place in a $CO_2$ incubator, in an atmosphere at a $CO_2$ concentration of 1-10%, preferably 2-5% and more preferably about 5%, at 30-40° C., preferably 35-37.5° C. and more preferably about 37° C. The culture period may be, for example, 1-4 weeks, preferably 1-3 weeks, and more preferably about 2 weeks. The medium is freshly exchanged every 1-3 days.

In this manner, the hepatocytes are brought into contact with the TGFβ-receptor inhibitor, and optionally the GSK3 inhibitor and/or the ROCK inhibitor so as reprogram the hepatocytes into hepatic stem/progenitor cells. Although mature hepatocytes are generally not considered to proliferate in vitro, they were found to proliferate by about 15 times by 2 weeks of culture as described in the examples below, for example, when primary rat mature hepatocytes were cultured with A-83-01 as the TGFβ-receptor inhibitor (A) in combination (YAC) with CHIR99021 as the GSK3 inhibitor (C) and Y-27632 as the ROCK inhibitor (Y). Moreover, when primary rat mature hepatocytes seeded at a low density ($1\times10^2$ cells/cm$^2$) were cultured in the presence of YAC and proliferation for each single cell was examined by low-speed imaging, about 25% of the single cells proliferated to 5 or more cells during 5 days of culture, that is, Day 2 to 6 following contact with YAC, showing a significant increase as compared to that in the absence of YAC (about 1.4%).

Herein, the term "hepatic stem/progenitor cells" (also referred to as "LSC") refers to cells that: have (a) self-regeneration ability; and (b) bipotential ability to differentiate into both hepatocytes and biliary epithelial cells. Herein, the term "biliary epithelial cells" (also referred to as "BEC") refers to cells that express cytokeratin 19 (CK19) and GRHL2 as BEC markers. The hepatic stem/progenitor cells (LSC) also comprise fetal liver hepatoblast and oval cells that emerge upon liver damage.

According to one preferable embodiment, in addition to the features (a) and (b) above and similar to conventionally known LSC, LSC obtained by the reprogramming method of the present invention (c) express epithelial cell adhesion molecule (EpCAM) as a surface antigen marker but do not express delta homolog 1 (Dlk1) expressed by other known LSC. Thus, LSC of the present invention can be said to be novel LSC. In addition, according to one embodiment, LSC of the present invention do not express leucine-rich repeat-containing G protein-coupled receptor 5 (LGR5) and FoxL1 which are known LSC markers.

LSC of the present invention further has one or more of the following features.

(d) the apparent growth rate does not slow down for at least 10 passages, preferably 20 passages or more.

(e) differentiation potency into hepatocytes and BEC is retained for at least 10 passages, preferably 20 passages or more.

(f) nuclear cytoplasmic (N/C) ratio is higher than that of hepatocytes.

(g) expressions of one or more LSC marker genes selected from the group consisting of α-fetoprotein (AFP), SRY-box (Sox) 9, EpCAM, Thy-1/CD90, hepatocyte nuclear factor 1 homeobox B (HNF1β), forkhead box J1 (FoxJ1), HNF6/one cut-1 (OC1), CD44, integrin α-6 (A6) and CK19 gene are increased compared to hepatocytes.

(h) expressions of one or more proteins selected from the group consisting of AFP, CD44, EpCAM, CK19, Sox9, A6 and CD90 are increased compared to hepatocytes.

According to a preferable embodiment, LSC of the present invention have all of the above-described features (d)-(h).

Accordingly, LSC can be induced from hepatocytes by bringing the hepatocytes into contact with a TGFβ-receptor inhibitor, and preferably further with a GSK3 inhibitor and/or a ROCK inhibitor.

Therefore, the present invention also provides an agent for inducing LSC from hepatocytes, comprising a TGFβ-receptor inhibitor. Preferably, a LSC inducer of the present invention is a combined agent of a TGFβ-receptor inhibitor with a GSK3 inhibitor and/or a ROCK inhibitor, and more preferably a combined agent of a TGFβ-receptor inhibitor with a GSK3 inhibitor and a ROCK inhibitor.

While the TGFβ-receptor inhibitor, the GSK3 inhibitor and the ROCK inhibitor can directly be used as a LSC inducer, they may also be made into a liquid agent by dissolving them in a suitable solvent. Alternatively, these inhibitors can be made into a kit by combining with the above-described medium for inducing LSC from hepatocytes.

2. Maintenance/Proliferation of LSC

The LSC of the present invention obtained as described above can efficiently be maintained/proliferated by passaging them in the presence of a TGFβ-receptor inhibitor, a GSK3 inhibitor and a ROCK inhibitor:

(i) on a collagen- or Matrigel-coated culture vessel for the first to fourth passages; and (ii) on a Matrigel-coated culture vessel for the fifth passage and so forth.

As the culture vessel, a culture vessel similar to one used for inducing LSC from hepatocytes can be used. The culture vessels used for the first to fourth passages are coated with collagen or Matrigel.

Once the primary LSC obtained as described above reach 70-100% confluency, they are seeded onto this collagen- or Matrigel-coated culture vessel at a density of $10^3$-$10^5$ cells/$cm^2$. As the medium, the medium described for induction culture of LSC can similarly be used. The concentrations of the TGFβ-receptor inhibitor, the GSK3 inhibitor and the ROCK inhibitor added can also suitably be selected from the concentration ranges described above for induction culture of LSC. The culture temperature and the $CO_2$ concentration also follow the conditions for induction culture of LSC. Once 70-100% confluency is reached, the cells are treated with trypsin to be dissociated, and passaged.

For the fifth passage and so forth, a Matrigel-coated culture vessel is used. Stable LSC can be obtained after about 5-8 passages. After 10 passages or more, cloning can be conducted by a routine procedure.

As described above, the TGFβ-receptor inhibitor, the GSK3 inhibitor and the ROCK inhibitor are added to the medium not only for LSC induction culture but also for maintenance/proliferation culture. Thus, the present invention also provides an agent for maintaining/proliferating LSC, comprising a TGFβ-receptor inhibitor, a GSK3 inhibitor and a ROCK inhibitor.

3. Redifferentiation from LSC into Hepatocytes

Induction of LSC to redifferentiate into hepatocytes may be carried out by a method known per se. Such method can be, for example, a method of culturing in a culture solution added with oncostatin M (OsM), dexamethasone (Dex), hepatocyte growth factor (HGF) or the like (Journal of Cellular Physiology, Vol. 227(5), p. 2051-2058 (2012); Hepatology, Vol. 45(5), p. 1229-1239 (2007)), or a method combined with a Matrigel overlaying method (Hepatology 35, 1351-1359 (2002)). The medium for inducing differentiation into hepatocytes may or may not be added, but preferably added, with a TGFβ-receptor inhibitor, a GSK3 inhibitor or a ROCK inhibitor.

The hepatocytes obtained by inducing differentiation of LSC of the present invention have a bile canaliculus-like structure typical of mature hepatocytes, and thus can accumulate drug metabolites in the canaliculi. In addition, they express an ABC transporter such as MRP2 protein in the cell membrane. Moreover, they can exert a series of hepatic functions such as secretory expression of albumin, glycogen accumulation, and cytochrome p450 (CYP) drug-metabolizing enzyme activity. Specifically, LSC of the present invention can redifferentiate into functional hepatocytes.

4. Induction of Differentiation of LSC into BEC

Induction of differentiation of LSC into BEC can be carried out by a method known per se. Such method can be, for example, a method in which collagen gel is used for culturing in a medium containing EGF and insulin-like growth factor 2 (IGF2).

The present inventors newly found a method for differentiating LSC of the present invention to form a bile duct-like structure with good reproducibility. Accordingly, the present invention also provides a method for inducing BEC from LSC. The BEC induction method of the present invention comprises the steps of:

(i) culturing LSC of the present invention on feeder cells at low density in the presence of a TGFβ-receptor inhibitor, a GSK3 inhibitor and a ROCK inhibitor; and (ii) further culturing the cells obtained in step (i) in a medium containing Matrigel.

The feeder cells used in step (i) is not particularly limited and any cells that are generally used for the purpose of supporting maintenance and culture can be used. For example, they may be mouse fetal-derived fibroblasts (MEF) and STO cells (ATCC, CRL-1503), preferably MEF.

Herein, the term "low density" refers to a density lower than the cell density generally used for the purpose of supporting maintenance and culture, which is, for example, a cell density in a range of $1\times10^3$-$5\times10^4$ cells/$cm^2$, and preferably $5\times10^3$-$3\times10^4$ cells/$cm^2$. A culture vessel for seeding the feeder cells may be one that is coated with a cell supporting substrate such as collagen or gelatin. The primary or passaged LSC of the present invention are treated with trypsin to be dissociated, resuspended in a medium containing a TGFβ-receptor inhibitor, a GSK3 inhibitor and a ROCK inhibitor, and seeded on the feeder cells at a cell density of $10^4$-$10^5$ cells/$cm^2$. If necessary, the medium may be added with a serum. On the following day, the medium is replaced with a maintenance medium for pluripotent stem cells such as mTeSR™1 (Stemcell Technologies), and subjected to culture in the presence of a TGFβ-receptor inhibitor, a GSK3 inhibitor and a ROCK inhibitor for 3-10 days, preferably 4-8 days. The medium is freshly exchanged every 1-3 days. Subsequently, the medium is exchanged with a medium containing Matrigel and further subjected to culture for 3-10 days, preferably 4-8 days. The medium is freshly exchanged every 1-3 days. The concentration of the Matrigel added to the medium can suitably be selected in a range of 1-5%, preferably 1-3%. With a total of about 1-3 weeks of culture, a bile duct-like structure is formed where the cells are expressing CK19 and GRHL2 as BEC markers at high levels. Moreover, gene and protein expressions of aquaporins such as AQP1 and AQP9 and ion channels such as CFTR and AE2 are increased. In addition, strong expression of ZO-1 as a tight junction marker is observed in the lumen of the duct structure. Furthermore, since these cells have the ability of transporting water and the ability of transporting and accumulating drug metabolites in the lumen, LSC of the present invention can differentiate into functional BEC.

5. Application of LSC of the Present Invention

The hepatocytes redifferentiated from LSC of the present invention as described in Item 3 above can be utilized, for example, for assessing metabolism and hepatotoxicity of a test compound.

Conventionally, animal models or the like have been used for the assessment of metabolism and hepatotoxicity of a test compound, but there are problems like limitation in the number of the test compounds that can be assessed at one time and assessments obtained with animal models or the like being unable to directly be applied to human. Therefore, an assessment method using a human hepatoma cell line or a primary culture of normal human hepatocytes has been employed. Since a human hepatoma cell line, however, is a cancer cell, assessment obtained with the human hepatoma cell line may possibly be inapplicable to normal human hepatocytes. In addition, the primary cultures of normal human hepatocytes are associated with problems in terms of stable supply and cost. Moreover, cell lines obtained by immortalizing primary cultures of normal human hepatocytes are shown to have lower CYP3A4 activity as compared to those not immortalized (International Journal of Molecular Medicine 14: 663-668, 2004, Akiyama I. et al.). These problems may be solved by utilizing hepatocytes produced according to the method of the present invention.

Thus, the present invention also provides a method for assessing metabolism of a test compound. According to this method, a test compound is brought into contact with hepatocytes produced by the method of the present invention. Then, metabolism of the test compound brought into contact with the hepatocytes is measured.

The test compound used with the present invention is not particularly limited. Examples include, but not limited to, a xenobiotic substance, a natural compound, an organic compound, an inorganic compound, a protein, a single compound such as a peptide, an expression product from a compound library or a gene library, a cell extract, a cell culture supernatant, a fermentative microbial product, a marine organism extract and a plant extract.

Examples of the xenobiotic substance include, but not limited to, candidate compounds for drugs and food, existing drugs and food, and a xenobiotic substance of the present invention comprises any substance as long as it is a foreign matter to the living body. More specific examples include Rifampin, Dexamethasone, Phenobarbital, Ciglirazone, Phenytoin, Efavirenz, Simvastatin, β-Naphthoflavone, Omeprazole, Clotrimazole and 3-Methylcholanthrene.

Contact between the hepatocytes and a test compound is usually carried out by adding the test compound to a medium or a culture solution, but it is not limited thereto. If the test compound is a protein or the like, a DNA vector expressing said protein may be introduced into the cells to make contact therewith.

The metabolism of the test compound can be measured by a method well known to those skilled in the art. For example, the test compound is judged to have been metabolized if a metabolite of the test compound is detected. Additionally, the test compound is also judged to have been metabolized if expression of an enzyme gene such as CYP (cytochrome p450), MDR or MRP is induced or activity of such enzyme is increased upon contact with the test compound.

The present invention also provides a method for assessing hepatotoxicity of a test compound. According to this method, a test compound is brought into contact with hepatocytes produced by the method of the present invention. Then, the degree of damage in the hepatocytes brought into contact with the test compound is measured. The degree of damage can be measured, for example, by using the viability of the hepatocytes or a liver damage marker such as GOT, GPT or the like as an indicator.

For example, a test compound is judged to have hepatotoxicity if viability of the hepatocytes is decreased upon adding the test compound to the culture solution of the hepatocytes, whereas a test compound is judged to have no hepatotoxicity when there is no significant change in the viability. Moreover, for example, a test compound is judged to have hepatotoxicity if GOT or GPT in the culture solution of the hepatocytes is increased after addition of the test compound to the culture solution, whereas a test compound is judged to have no hepatotoxicity when there is no significant change in GOT or GPT.

Here, a compound whose presence or absence of hepatotoxicity is already known can be used as a control so as to assess whether or not a test compound has hepatotoxicity in a more accurate way.

As shown in the examples described below, LSC of the present invention can be transplanted into an immunodeficient mouse with chronic liver damage so as to exert liver regeneration ability comparative to transplantation of primary mature hepatocytes. Thus, the present invention also provides an agent for ameliorating liver damage, comprising LSC of the present invention.

If necessary, LSC of the present invention may be purified before use by flow cytometry using an antibody for surface antigen marker EpCAM. LSC can be suspended in a suitable isotonic buffer (for example, PBS) to be formulated. If necessary, a pharmaceutically acceptable additive can further be contained. Although the LSC suspension may differ depending on the type of the liver disease, seriousness of the liver damage or the like, for example, $10^8$-$10^{11}$ cells can be transplanted by intraportal administration, intrasplenic administration or the like in a case of an adult.

Hereinafter, the present invention will be described more specifically by way of examples, although the present invention should not be limited to these examples in any way.

EXAMPLES

Procedures of Experiments

Isolation of Mature Hepatocytes

Adult rat hepatocytes were isolated from a 10-20-week-old female Wistar rat (CLEA Japan, Shizuoka) by Seglen procedure. In summary, following preliminary perfusion with a $Ca^{2+}$-free Hanks'/EGTA solution via the portal vein, the liver was perfused with about 400 mL of 0.05% collagenase-containing Hank's solution at 25-30 mL/min. The excised liver was mechanically digested using scissors, and further digested in a 0.025% collagenase solution at 37° C. for 15 minutes. Subsequently, the digested liver was filtrated through sterilized cotton mesh twice and centrifuged at 57 g for a minute to collect the cell suspension. The cell suspension was filtrated through a 60 μm stainless double mesh cell strainer (Ikemoto Scientific Technology, Tokyo) to remove undigested cell mass, and centrifuged at 57 g for a minute to collect the filtrate. Percoll (GE healthcare) was used for centrifugation at 57 g for 10 minutes to remove the dead cells, and then the cells were washed with E-MEM twice by centrifugation at 57 g for 2 minutes. The thus-purified hepatocytes were used in various experiments.

Primary Culture of Mature Hepatocytes

As a basal medium for culturing mature hepatocytes, a small hepatocyte culture medium (SHM), namely, 2.4 g/L NaHCO$_3$ and L-glutamine-containing DMEM/F12 (Life Technologies, Carlsbad, Calif.) added with 5 mM HEPES (Sigma, St. Louis, Mo.), 30 mg/L L-proline (Sigma), 0.05% BSA (Sigma), 10 ng/mL epithelial cell growth factor (Sigma), insulin-transferrin-selenium (ITS)-X (Life Technologies), $10^{-7}$M dexamethasone (Dex), 10 mM nicotinamide (Sigma), 1 mM ascorbic acid-2-phosphate (Wako Pure Chemical, Tokyo) and an antibiotic-antimycotic solution (100 U/mL penicillin and 100 mg/mL streptomycin and 0.25 mg/mL amphotericin B) (Life Technologies) was used. The purified fresh rat mature hepatocytes were suspended in SHM added or not added with any combination of the following four low-molecular weight inhibitors: 10 µM Y-27632 (WAKO), 1 µM PD0325901 (Axon Medchem, Groningen, Netherland), 0.5 µM A-83-01 (TOCRIS, Bristol, UK) and 3 µM CHIR99021 (Axon Medchem), and seeded onto a Collagen Type I-coated plate (AGC Techno Glass, Shizuoka) at $1\times10^4$ cells/cm$^2$. The medium was exchanged the day after the seeding and thereafter the medium was exchanged every other day.

Passage of MH-LSC

On the 14th day of primary culture, cells cultured in the presence of YAC were treated with trypsin to be collected, and seeded onto a YAC-added SHM at $3\times10^4$ cells/cm$^2$. For the first four passages, the cells were cultured on a Matrigel- or collagen-coated plate. For the fifth and the following passages, the cells were basically cultured on a Matrigel-coated plate. CELLBANKER (registered trademark) 1 (Takara Bio, Otsu) was used to prepare a cryopreserved stock. At least 10 passages later, MH-LSC were cloned using Stem Cell Cutting Tool (Veritas, Tokyo).

Low-Speed Imaging at Low Cell Density

The primary hepatocytes were seeded onto a collagen-coated 35-mm plate (IWAKI) in the presence or the absence of YAC at $1\times10^2$ cells/cm$^2$. On the first day, the medium was exchanged. After the second medium exchange, BZ9000 All-in-One Fluorescence Microscope (Keyence, Osaka) was used to perform low-speed imaging. Phase difference images were taken every 30 minutes for 300 times from Day 2 to Day 6, and movies were made for every analytical field. Next, individual cells were traced throughout the imaging period to determine the final cell count originating from the cells of interest. Additionally, the total number of apoptotic cells originating from the individual cells was also counted to quantitate apoptotic frequency as total apoptotic cells/ original total cell count (counted at the beginning of low-speed imaging).

Quantitative RT-PCR

Total RNA was isolated from the hepatocytes and LSC cells using miRNeasy Mini Kit (QIAGEN). Reverse transcription reaction was carried out using High-Capacity cDNA Reverse Transcription Kit (Life Technologies) following the manufacturer's guideline. The resulting cDNA was used as a template to perform PCR with Platinum SYBR Green qPCR SuperMix UDG (Invitrogen). The expression level of the target gene was normalized with β-actin as the endogenous control.

Immunocytochemistry, Immunohistochemistry and PAS Staining

The cells were fixed on ice with cold methanol (−30° C.) for 5 minutes. The resultant was incubated with a blocking solution (Blocking One) (Nacalai Tesque, Kyoto) at 4° C. for 30 minutes, and then the cells were incubated with primary antibody at room temperature for an hour or at 4° C. overnight. Then, Alexa Fluor 488 or Alexa Fluor 594-labeled secondary antibody (Life Technologies) was used to detect the primary antibody. The nuclei were co-stained with Hoechst 33342 (Dojindo).

The tissue sample was fixed with formalin and paraffin-embedded. After dewaxing and rehydration, the specimen was boiled in a 1/200 diluted ImmunoSaver (Nisshin EM, Tokyo) at 98° C. for 45 minutes to retrieve the heat-induced epitope. Then, the specimen was treated with 0.1% Triton-X 100 for membrane permeabilization. Following treatment with a blocking reagent (Nacalai Tesque) at 4° C. for 30 minutes, the specimen was incubated with a primary antibody at room temperature for an hour. These sections were stained using ImmPRESS IgG-peroxidase kit (Vector Labs) and metal-enhanced DAB substrate kit (Life Technologies) following the manufacturers' instructions. After counterstaining with hematoxylin, the specimen was dehydrated and mounted.

Periodic acid-Schiff (PAS) staining was performed using PAS kit (Sigma-Aldrich) to detect glycogen in the presence and the absence of salivary diastase pretreatment.

Induction of Hepatocytes from MH-LSC

Day 14 primary MH-LSC or cells from Rep-LS cell line were treated with trypsin and collected. The cells were suspended in SHM+YAC added with 5% FBS, and seeded onto a collagen-coated plate at $3.75\times10^4$-$5\times10^4$ cells/cm$^2$. The medium was exchanged with SHM+YAC on Day 1 and thereafter culture took place for 2 days. Next, for hepatocyte differentiation, the medium was replaced with SHM+YAC added with 20 ng/mL oncostatin M (OsM) (Wako) and $10^{-6}$M Dex, and the cells were cultured for 6 days while exchanging the medium every two days. On Day 6 following the beginning of the induction, the cells were overlaid with a 1:7 mixture of Matrigel (Corning) and the above-described hepatocyte induction medium and cultured for another two days. At the end of the hepatocyte induction, Matrigel was suctioned to be removed, and the cells were used in various function assays. As a negative control, the cells were maintained in SHM+YAC throughout the corresponding culture period.

Induction of Bile Duct from MH-LSC

Prior to MH-LSC seeding, mouse fetal fibroblasts (MEF) having cell cycle arrested were seeded onto a collagen-coated 12-well plate at $5\times10^4$ cells/well. On the following day, Day 14 primary MH-LSC were treated with trypsin and collected, resuspended in SHM+YAC added with 5% FBS, and seeded on a pre-seeded MEF at $5\times10^5$ cells/well. On the following day, the medium was exchanged with YAC-containing mTeSR™1 (Stemcell Technologies) (mTeSR1+YAC) to begin bile duct induction, and the culture was continued for 6 days while exchanging the medium every two days. On Day 6 following the beginning of the induction, the medium was replaced with mTeSR1+YAC added with 2% Matrigel and culture was further continued for 6 days while exchanging the medium every two days. The bile duct induction was completed after a total of 12 days of culture and the resulting cells were used in an assay. As a negative control, the cells were cultured in SHM+YAC on MEF throughout the corresponding culture period.

Albumin Secretion Assay

Rat Albumin ELISA Quantitation Set (Bethyl, Montgomery, Tex.) was used to measure the albumin (ALB) concentration by ELISA. In order to monitor change in the ALB secretion ability with time, the culture supernatants were sampled every two days for the first 6 days of hepatocyte induction. In order to determine the ALB secretion ability after the completion of hepatocyte induction, the overlaying Matrigel was suctioned to be removed on Day 8. Half of these cells were collected for measuring the DNA content while the other half were added with a fresh medium to culture for another 2 days. On Day 10, the culture supernatant was corrected to measure the ALB secreted during Day 8 to 10, which was normalized with the DNA content on Day 8. The DNA content was measured using DNA Quantity Kit (Cosmo Bio, Tokyo).

Determination of CYP1A Activity

In order to induce CYP1A activity, cells on Day 8 of hepatocyte induction were treated with 5 μM 3-methylcholanthrene (3-MC) (Sigma) for 4 days (the medium was exchanged on the second day). The control cells were treated only with DMSO as a solvent. Four days later, P450-Glo CYP1A1 Assay (Luciferin-CEE) was used to determine CYP1A activity. According to the manufacturer's instruction, this kit can detect CYP1A2 activity more efficiently than CYP1A1 activity. Following CYP1A activity, the DNA content of the cells was measured to normalize the CYP activity. In order to examine the responsiveness to 3-MC, fold changes in activity were calculated as [mean luminescence in the presence of 3-MC/mean luminescence in the absence of 3-MC] for 3 wells/condition in each experiment to determine an average value for five independent experiments. In two experiments, total RNA was isolated to assess the gene expression levels of CYP1A1 and CTP1A2.

Fluorescein Diacetate Assay

For hepatocyte induction, the cells were incubated in a medium containing 2.5 μg/mL fluorescein diacetate (FD) (Sigma) in a $CO_2$ incubator for 15 minutes. After replacing the medium with Hanks' balanced salt solution (HBSS) (Life Technologies), metabolized fluorescein was detected under a fluorescence microscope. For bile duct induction, following 15 minutes of incubation, the medium was freshly exchanged, and culture was continued for another 30 minutes to induce transportation of metabolized fluorescein to the lumen. Then, the medium was replaced with HBSS to observe fluorescein distribution under a fluorescence microscope.

Secretion Assay

The cells that underwent bile duct induction were cultured for 30 minutes in the presence of $2 \times 10^{-7}$ M rat selectin (Wako) to observe lumen expansion of the bile duct-like structure.

Cell Nuclei Count

The cells fixed with methanol were stained with Hoechst 33342 that was 1/1000 diluted in PBS(−) to count the nuclei using Cellomics' ArrayScan (R) VTI System (Life Technologies) according to the manufacturer's instruction.

Induction of LSC from Cryopreserved Hepatocytes

Cryopreserved rat mature hepatocytes (Biopredic) were melted according to the manufacturer's instruction. As a basal medium for culturing the cryopreserved rat hepatocytes, a small hepatocyte culture medium (SHM), namely, 2.4 g/L $NaHCO_3$ and L-glutamine-containing DMEM/F12 (Life Technologies, Carlsbad, Calif.) added with 5 mM HEPES (Sigma, St. Louis, Mo.), 30 mg/L L-proline (Sigma), 0.05% BSA (Sigma), 10 ng/mL epithelial cell growth factor (Sigma), insulin-transferrin-selenium (ITS)-X (Life Technologies), $10^7$M dexamethasone (Dex), 10 mM nicotinamide (Sigma), 1 mM ascorbic acid-2-phosphate (Wako Pure Chemical, Tokyo) and antibiotic-antimycotic solution (100 U/mL penicillin, 100 mg/mL streptomycin and 0.25 mg/mL amphotericin B) (Life Technologies) was used. The melted cryopreserved rat mature hepatocytes were suspended in SHM added or not added with the following four low-molecular weight inhibitors: 10 μM Y-27632 (WAKO), 1 μM PD0325901 (Axon Medchem, Groningen, Netherland), 0.5 μM A-83-01 (TOCRIS, Bristol, UK) and 3 μM CHIR99021 (Axon Medchem), and seeded onto a Collagen Type I-coated plate (AGC Techno Glass, Shizuoka) at $1 \times 10^4$ cells/cm$^2$. The medium was exchanged the day after the seeding and thereafter the medium was exchanged every other day.

LSC Induction from Cryopreserved Human Hepatocytes

The cryopreserved human hepatocytes (Xenotech) were melted according to the manufacturer's instruction. SHM was used as a basal medium for culturing the cryopreserved human hepatocytes. Induction was carried out in the same manner as the above-described LSC induction from the cryopreserved rat mature hepatocytes except that three low-molecular weight inhibitors other than PD0325901 were used. The cryopreserved human hepatocytes used are shown in Table 1.

TABLE 1

| Lot ID | Age | Sex | Demographics | Supplier |
|---|---|---|---|---|
| HC1-14 | 55 | Male | Caucasian | Xenotech |
| HC3-14 | 45 | Male | Caucasian | Xenotech |
| HC5-25 | 56 | Male | Caucasian | Xenotech |

Passage of MH-LSC Induced from Cryopreserved Human Hepatocytes

The MH-LS induced from the cryopreserved human hepatocytes were passaged in the same manner as the above-described passage of MH-LSC.

Figure 2:
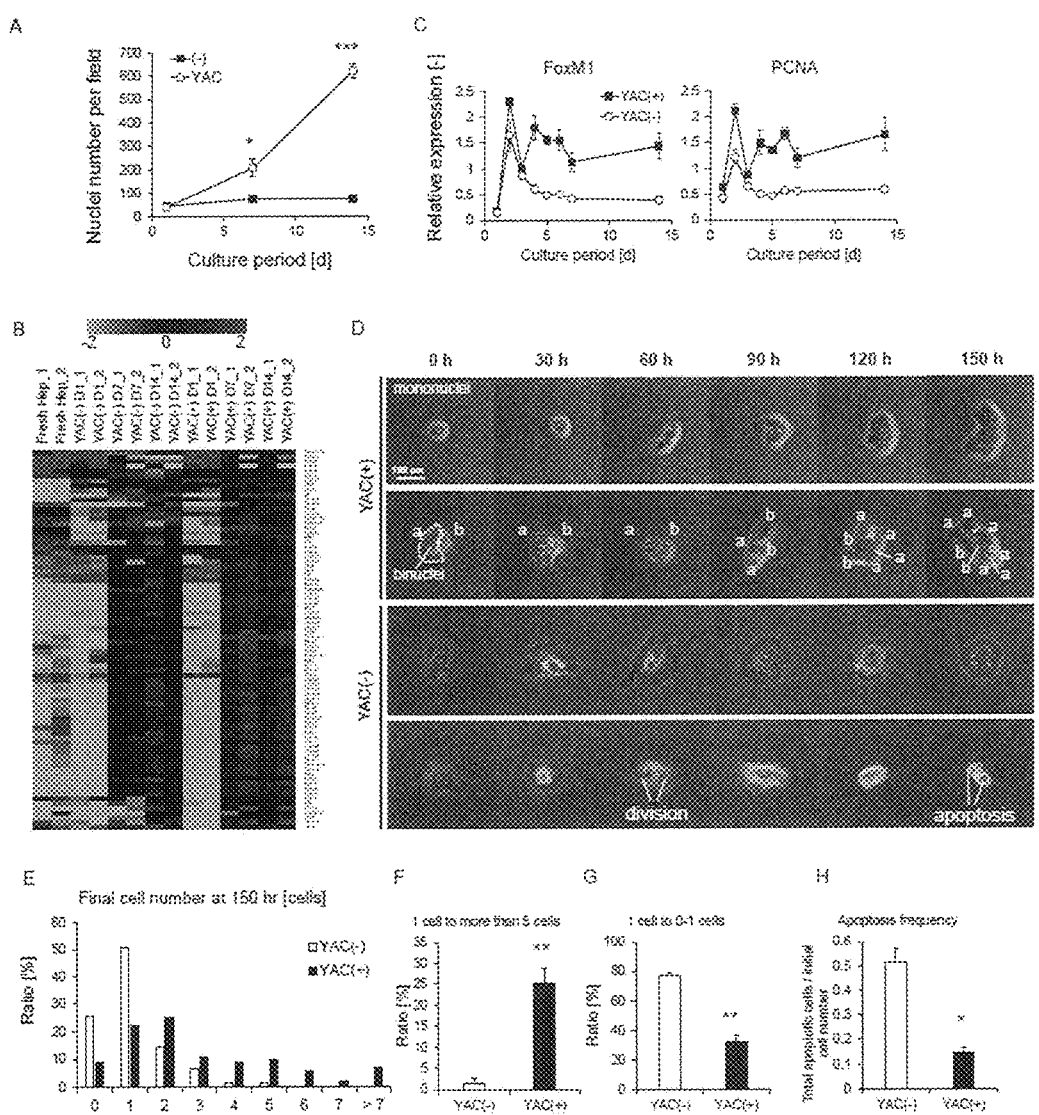
FIG. 2 Views showing proliferation of primary rat mature hepatocytes cultured in the presence and the absence of YAC.

Example 1: Low-Molecular Weight Inhibitor Induces Proliferation of Primary Mature Hepatocytes The present inventors and other groups have previously reported that a low-molecular weight inhibitor contributes to the induction and maintenance of pluripotency of stem cells (Hou et al., 2013; Kawamata and Ochiya, 2010). Furthermore, the present inventors revealed that the maintenance of breast cancer cells in vitro strongly depends on the presence of small molecules. Based on these findings, the present inventors examined whether a particular combination of these small molecules, namely, Rho kinase inhibitor Y-27632, mitogen-activated protein kinase (MEK) inhibitor PD0325901, type 1 transforming growth factor (TGF)-β-receptor inhibitor A-83-01 and glycogen synthase kinase-3 (GSK3) inhibitor CHIR99021, reprograms adult hepatocytes into a hepatic stem cell-like differentiation state. First, primary mature hepatocytes were isolated from a 10-20-week-old rat and cultured in the presence of all possible combinations of the above-mentioned four factors. Contrary to the general idea that mature hepatocytes do not proliferate in vitro, proliferation of the mature hepatocytes was clearly observed in the presence of some combinations of the four factors (FIGS. 1a and b). Among them, the combination of the three factors, i.e., Y-27632, A-83-01 and CHIR99021 (hereinafter, referred to as YAC) gave the strongest ability to proliferate the mature hepatocytes. Therefore, the effect of YAC on the mature hepatocytes was focused in the following experiments. The present inventors confirmed that YAC increased the number of cell nuclei by about 15 times during 2 weeks of culture (FIG. 2A). A microarray analysis revealed that the gene expression levels of the series of cell cycle markers were up-regulated in the presence of YAC on Day 7 (D7) and Day 14 (D14) of culture (FIG. 2B). The results from quantitative RT-PCR analysis confirmed that PCNA and FoxM1 were consistently expressed at a high level during the 2 weeks of mature hepatocyte culture under YAC stimulation (FIG. 2C). A frame photography analysis of sparsely seeded hepatocytes confirmed that the cells undergoing proliferation originated from cells having the form of typical mature hepatocytes (FIG. 2D). Moreover, some of the cells undergoing proliferation were originally binucleated cells (FIG. 2D), strongly suggesting that the mature hepatocytes were the origin of YAC-induced proliferating cells. On the contrary, proliferating cells hardly emerged under no YAC stimulation, and more cells resulted in apoptosis (FIG. 2D). The results from quantitative analysis showed clear shift in the cell count profile between the presence and the absence of YAC (FIG. 2E). In particular, the rate of single cells that produced 5 or more cells during 5 days of culture (from Day 2 to 6) was 1.39% in the absence of YAC whereas it remarkably increased to 25.1% in the presence of YAC (FIG. 2F). On the contrary, the rate of single cells that became 1 or less cell was 77.3% in the absence of YAC whereas it was only 4.30% in the presence of YAC (FIG. 2G). Moreover, frequency of apoptosis of the primary hepatocytes was more suppressed in the presence of YAC than in the absence of YAC (FIG. 2H).

Figure 3:
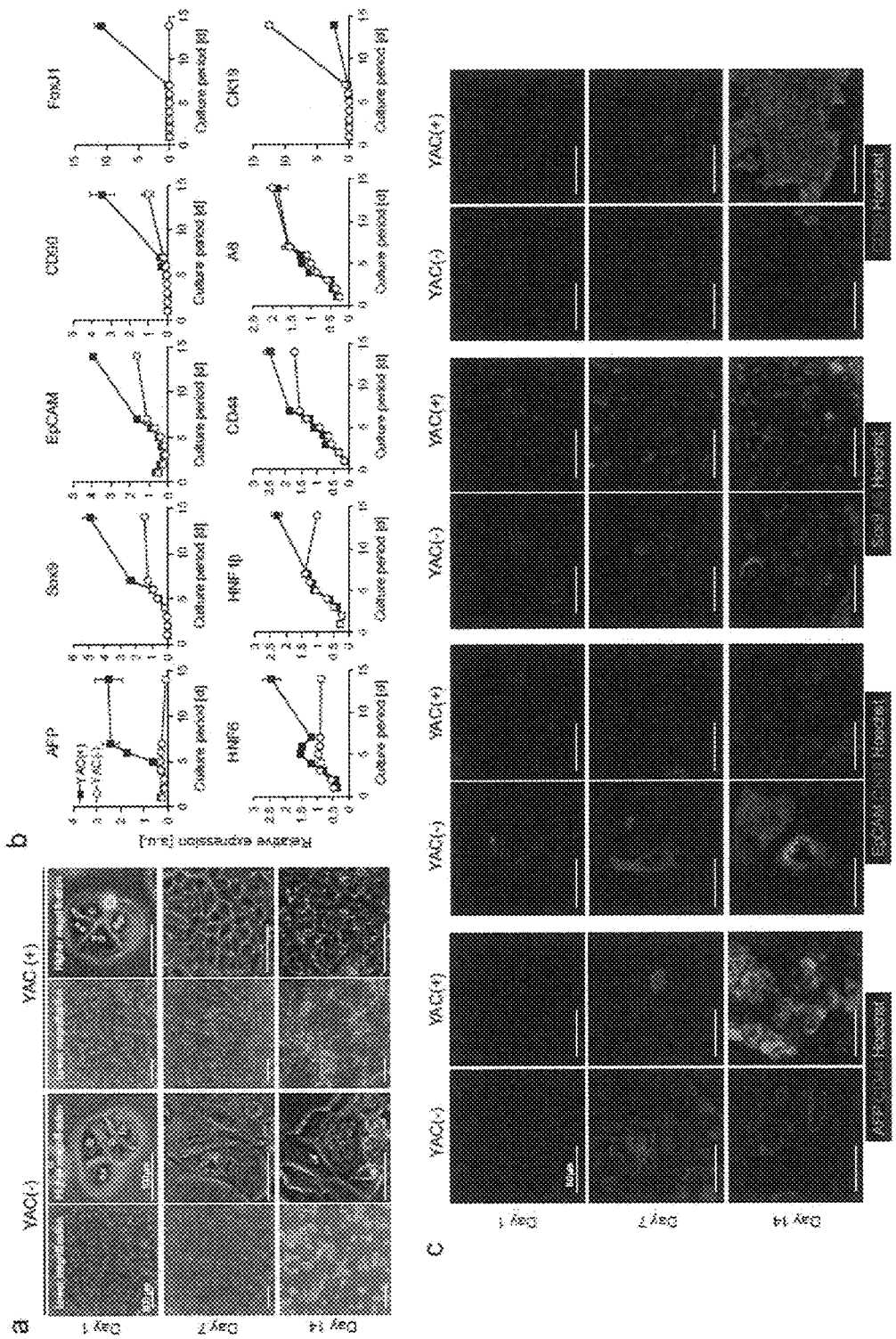
FIG. 3 Views showing N/C ratios and expressions of hepatic stem/progenitor cell markers in primary rat mature hepatocytes cultured in the presence and the absence of YAC.

Example 2: YAC-Induced Proliferating Cells are Similar to Hepatic Progenitor Cells YAC-induced proliferating cells showed a higher nuclear cytoplasmic (N/C) ratio compared to those of the primary hepatocytes on Day 0 and the cells under no YAC stimulation (FIG. 3a). Such property is characteristic of LSC including fetal hepatoblast and adult ovoid cells. Accordingly, the present inventors examined whether or not the YAC-induced proliferating cells were similar to LSC in terms of expression of a LSC marker. Results from a quantitative RT-PCR analysis showed that expression levels of a number of LSC markers including α-fetoprotein (AFP), SRY-box (Sox) 9, epithelial cell adhesion molecule (Ep-CAM), Thy-1/CD90, hepatocyte nuclear factor 1 homeobox B (HNF1β), forkhead box J1 (FoxJ1), HNF6/one cut-1 (OC1), CD44, integrin α-6 (A6) and CK19 were increased during 2 weeks of culture under YAC stimulation (FIG. 3b). The protein expression levels of AFP, CD44, EpCAM, CK19, Sox9, A6 and CD90 were confirmed to be increased by YAC stimulation (FIG. 3c). These results strongly suggest that YAC stimulation not only imparts proliferation ability to the mature hepatocytes but also at least partially imparts expression of LSC-specific markers as well. Accordingly, the present inventors termed the YAC-induced proliferating cells as mature hepatocyte-derived hepatic stem cell-like cells (MH-LSC). Next, the present inventors examined whether MH-LSC can differentiate into both hepatocytes and biliary epithelial cells (BECs).

Example 3: MH-LSC can Differentiate into Functional Hepatocytes

Figure 4:
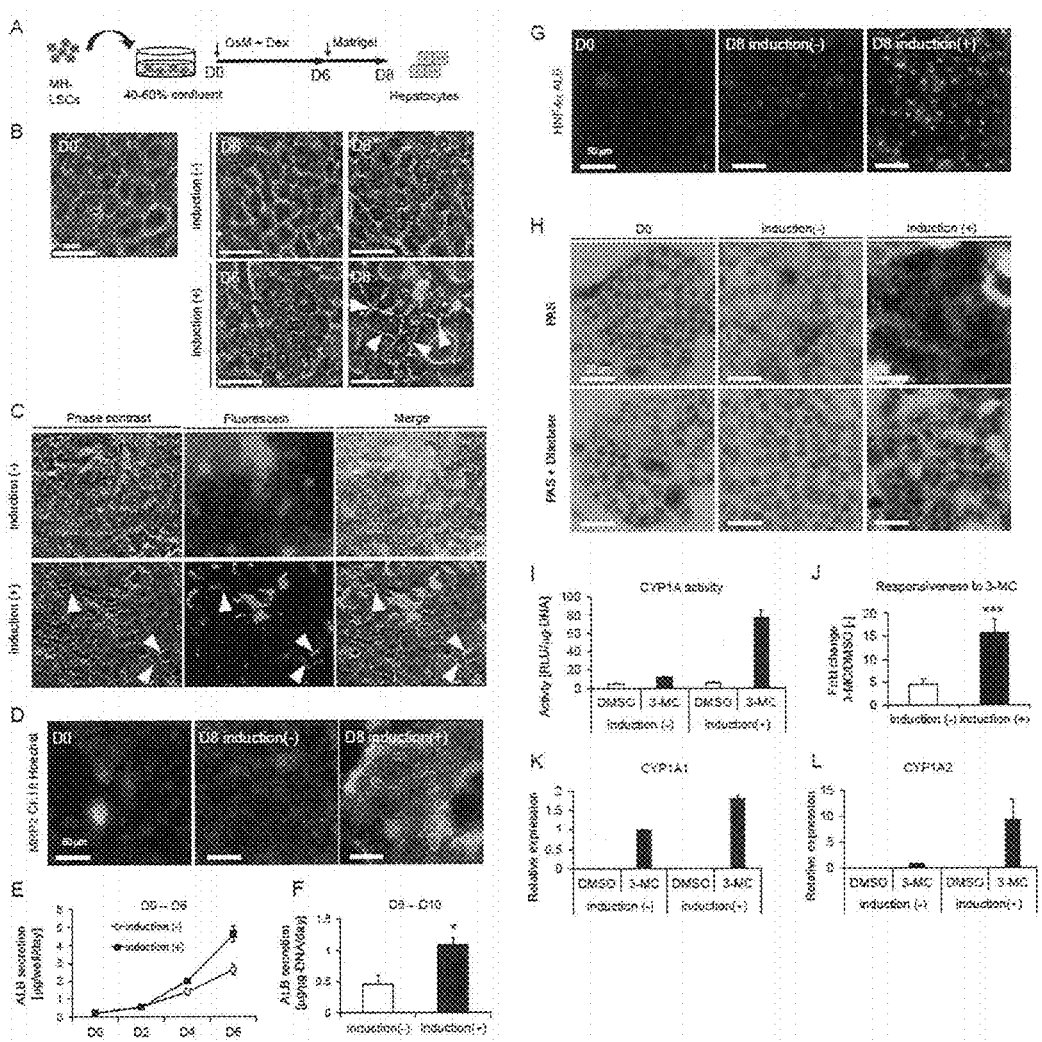
FIG. 4 Views showing that hepatic stem/progenitor cells derived from rat mature hepatocytes have redifferentiation potency into functional hepatocytes.
Figure 5:
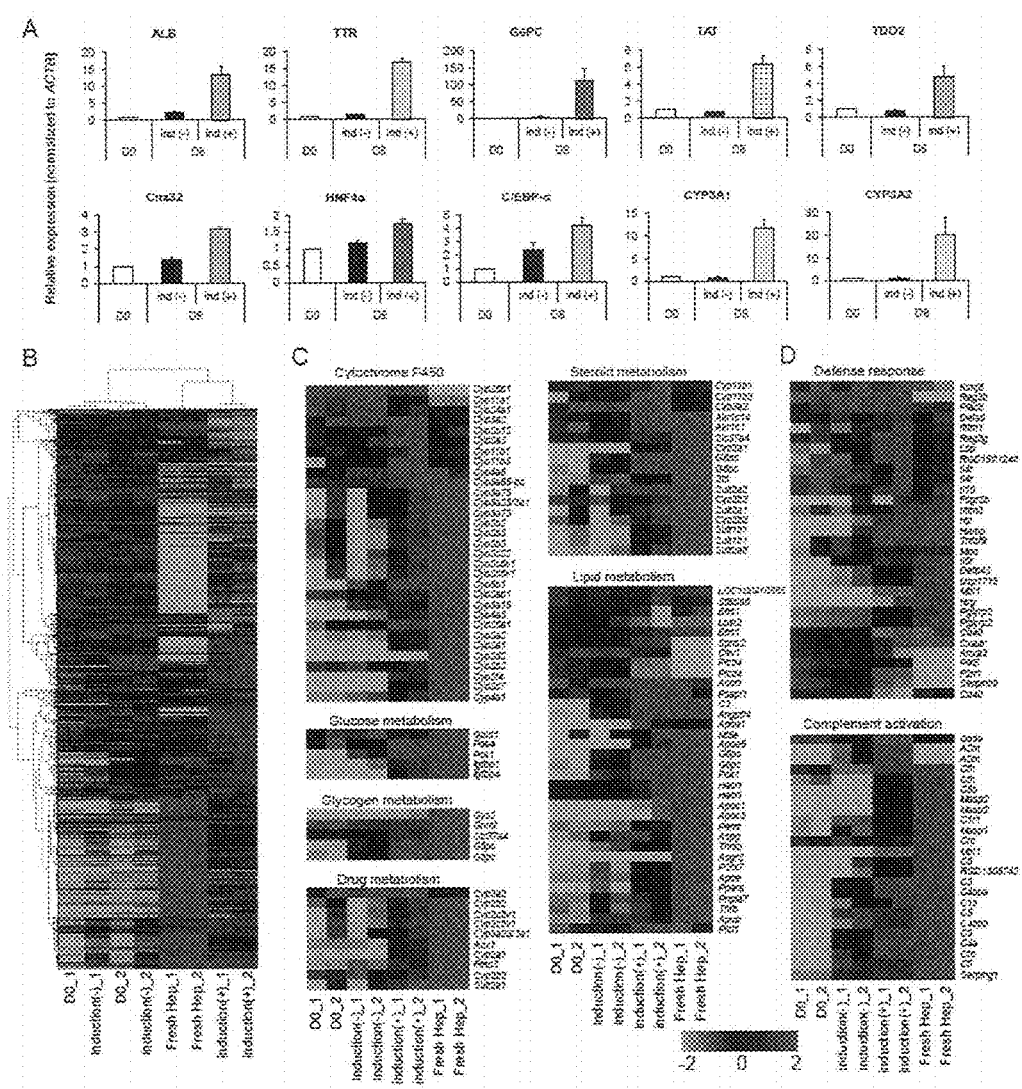
FIG. 5 Views showing results from a gene clustering analysis showing that hepatic stem/progenitor cells derived from rat mature hepatocytes have redifferentiation potency into functional hepatocytes.

The present inventors first examined whether or not MH-LSC have differentiation potency into hepatocytes using the previously reported hepatic maturity protocol (Kamiya et al., 2002) (FIG. 4A). Matrigel overlay on MH-LSC (referred to as Hep-i(+) cells) subjected to hepatic differentiation stimulation with oncostatin M (OsM) and dexamethasone (Dex) gave a typical mature hepatocyte-like form having a bile canaliculus-like structure (FIG. 4B). In fact, after fluorescein diacetate (FD) administration, metabolized fluorescein accumulated in the canaliculi formed with the Hep-i(+) cells (FIG. 4C). This phenomenon was neither observed in MH-LSC before hepatic induction nor in MH-LSC (Hep-i(−) cells) that were cultured for the same period without hepatic induction (FIG. 4C). Additionally, while Hep-i(+) cells expressed MRP2 protein in the cell membrane, neither MH-LSC nor Hep-i(−) cells expressed said protein (FIG. 4D). Furthermore, Hep-i(+) cells exerted a series of hepatic functions, namely, albumin (ALB) expression at protein level (FIG. 4E) and secretion thereof (FIGS. 4F and 4G), glycogen accumulation (FIG. 4H) and CYP1A activity (FIG. 4I), at higher levels than Hep-i(−) cells or undifferentiated MH-LSC. Importantly, not only CYP1A activity (FIGS. 4I and 4J) but also CYP1A1 and CYP1A2 gene expressions (FIGS. 4K and 4L) were efficiently induced in response to 3-methylcholanthrene (3-MC) stimulation. These findings can be supported by the gene clustering analysis using mRNA microarrays (FIG. 5A). In fact, the gene set involved in hepatic functions such as metabolic process and protective responses was up-regulated even in Hep-i(+) cells (FIG. 5B). Data from the microarrays was confirmed by quantitative RT-PCR (FIG. 5C). Importantly, most of the cell cycle-associated genes were down-regulated after the hepatic induction. Such gene expression pattern was a sharp contrast to that of undifferentiated MH-LSC. Therefore, MH-LSC are strongly suggested not to cause carcinogenic transformation by YAC stimulation.

Example 4: MH-LSC can Differentiate into Functional Biliary Epithelial Cells

Figure 6:
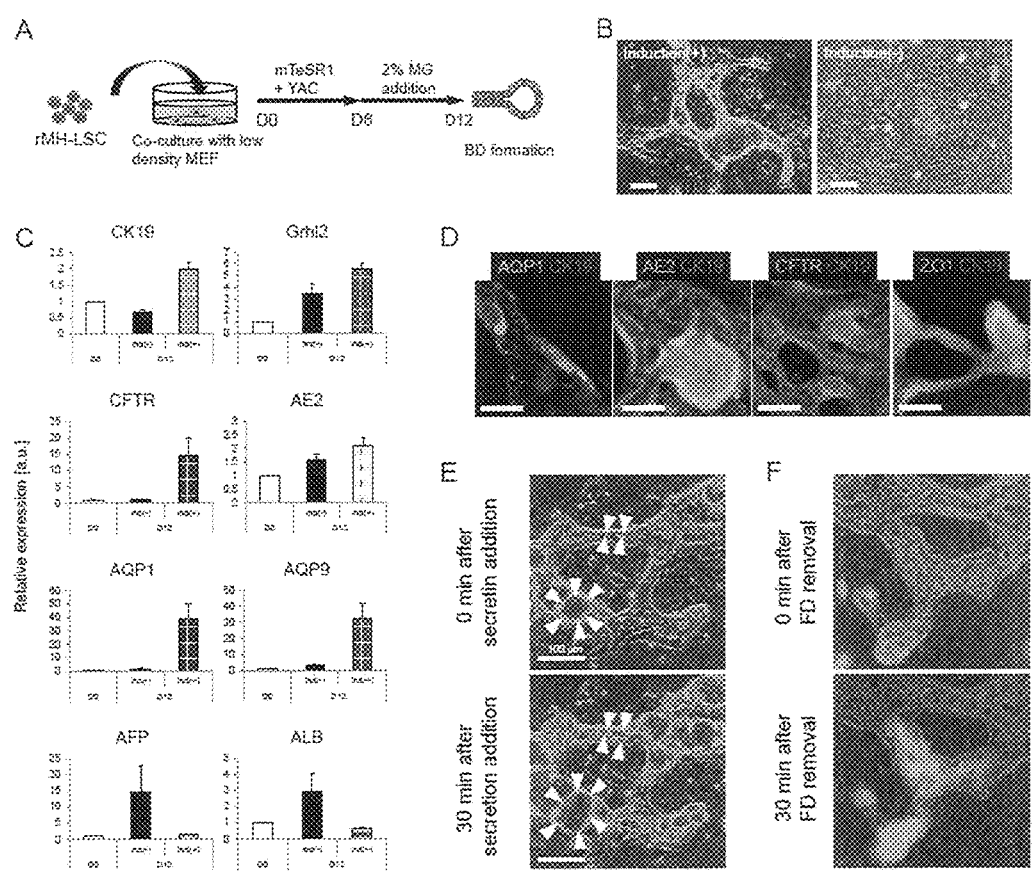
FIG. 6 Views showing that hepatic stem/progenitor cells derived from rat mature hepatocytes have redifferentiation potency into functional biliary epithelial cells.

The present inventors found that MH-LSC can also differentiate into biliary epithelial cells (BEC) besides differentiation potency into hepatocytes. In a preliminary experiment, the present inventors examined culture conditions that allow long-term culture of MH-LSC, and interestingly found conditions for imparting an ability to form a bile duct-like structure to MH-LSC. The present inventors slightly modified these conditions and succeeded in differentiating MH-LSC to form a bile duct-like structure with good reproducibility. The modified culture conditions consisted of 2 steps, that is, a step of coculturing MH-LSC on sparsely seeded mouse fetal fibroblasts (MEF) in a mTeSR1 medium for 6 days, and a step of culturing the cells obtained in the previous step in a 2% Matrigel-added mTeSR1 medium for another 6 days (FIG. 6A). While MH-LSC (referred to as BEC-i(+) cells) cultured under these conditions formed a duct structure, MH-LSC (BEC-i(−) cells) cultured on MEF in a basal MH-LSC maintenance medium showed usual single layer form (FIG. 6B). BEC-i(+) cells expressed BEC markers CK19 and GRHL2 at higher levels than BEC-i(−) cells and undifferentiated MH-LSC (FIG. 6C). It is noteworthy that two aquaporins AQP1 and AQP9 and two ion channels CFTR and AE2 were significantly up-regulated in BEC-i(+) cells (FIG. 6C), strongly suggesting that the cells differentiated functionally as a bile duct. On the other hand, BEC-i(−) cells naturally differentiated into hepatocyte-like cells as indicated by the increases in ALB and AFP expression levels (FIG. 6C). On the contrary, BEC-i(+) cells did not show an increase in expression of these hepatocyte marker genes (FIG. 6C), suggesting that they have committed to the BEC lineage. Results from immunocytochemistry analysis confirmed that BEC-i(+) cells expressed AQP1 on the apex side of the duct structure (FIG. 6D). AE2 and CFTR were also expressed in BEC-i(+) cells that formed a single-layer epithelium (FIG. 6D). Moreover, tight junction marker ZO-1 was expressed in the lumen of the duct structure (FIG. 6D). These results strongly suggest that the duct structure was functional. In fact, stimulation of BEC-i(+) cells with selectin induced expansion of the lumen (FIG. 6E), demonstrating that the cells had the ability of transporting water. Furthermore, the duct structure transported and accumulated metabolized fluorescein in the lumen in the presence of FD (FIG. 6F). To summarize, MH-LSC were shown to be capable of proliferating and differentiating into both hepatocytes and BEC, strongly suggesting similarity to genuine LSC in terms of phenotype.

Figure 7:
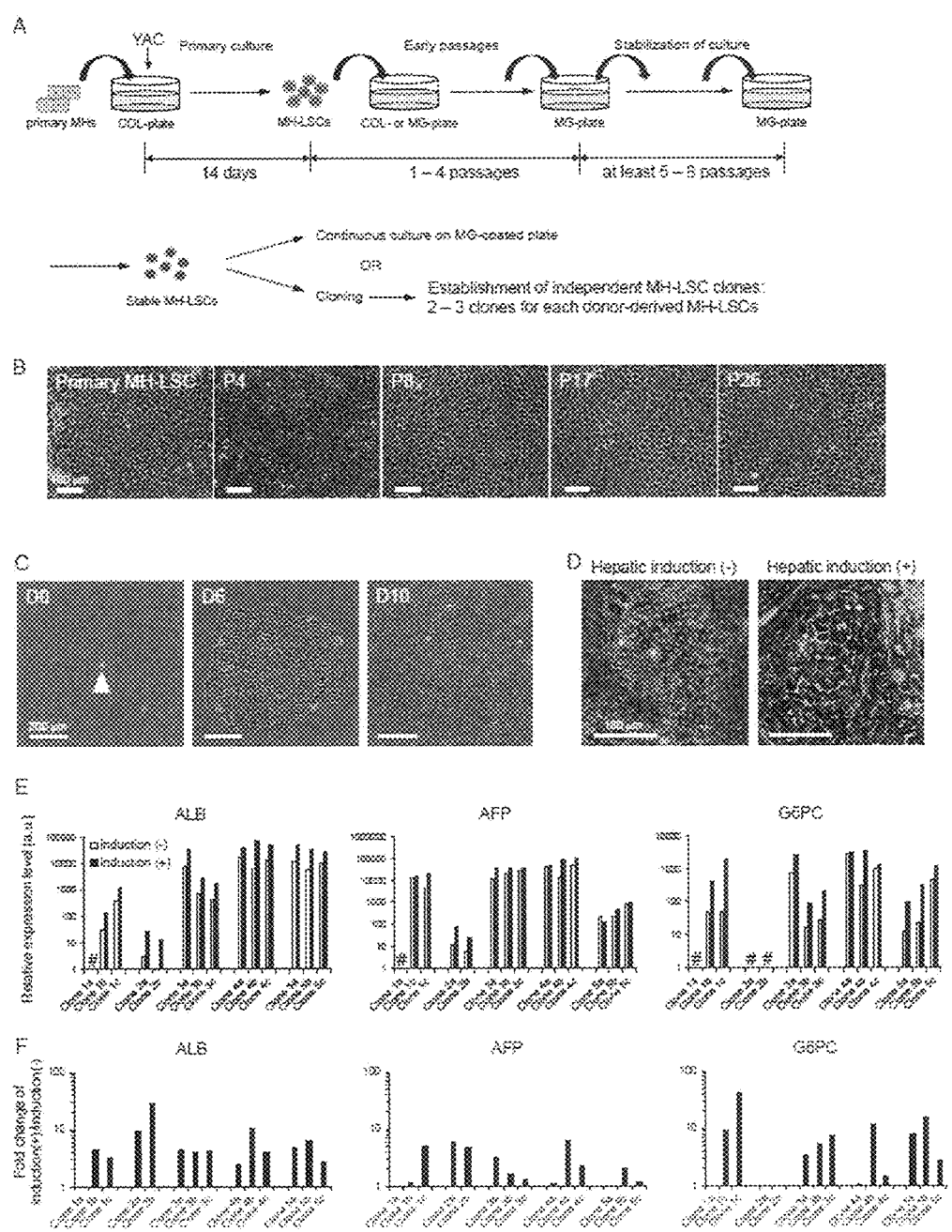
FIG. 7 Views showing that hepatic stem/progenitor cells derived from rat mature hepatocytes are capable of long-term passage without losing proliferation ability and redifferentiation potency into hepatocytes.

Example 5: Long-Term Culture of MH-LSC without Losing Efficient Hepatic Differentiation Potency In order to assess applicability of MH-LSC to liver regenerative medicine, the present inventors examined conditions that allow stable proliferation of MH-LSC over passages. As a result, they found that continuous passage of MH-LSC can be realized by coating the culture plate with Matrigel (FIG. 7A). In the first experiment, at least 26 passages of MH-LSC were confirmed without weakening the apparent proliferation ability (FIG. 7B). Moreover, proliferation was possible by cloning stably cultured MH-LSC (FIG. 7C). Then, 2-4 clones were established in each of the five independent experiments after about 10 passages. Hepatic functions of them were assessed by observation with a microscope and quantitative RT-PCR. In each experiment, clones showing an epithelium form were obtained (FIG. 7C). These cells exhibited mature hepatocyte-like form in response to the above-described hepatic induction (FIG. 4A) (FIG. 7D). Although gene expression levels of hepatocyte markers such as ALB, AFP and G6PC varied among the established clones (FIG. 7E), the expression levels of these genes increased in response to the hepatic induction in every clones (FIG. 7F). Accordingly, MH-LSC were stably proliferated under such culture conditions while retaining hepatic differentiation potency and established MH-LSC clones with good reproducibility.

Example 6: Regeneration Ability of MH-LSC in Chronically Injured Liver

Figure 8:
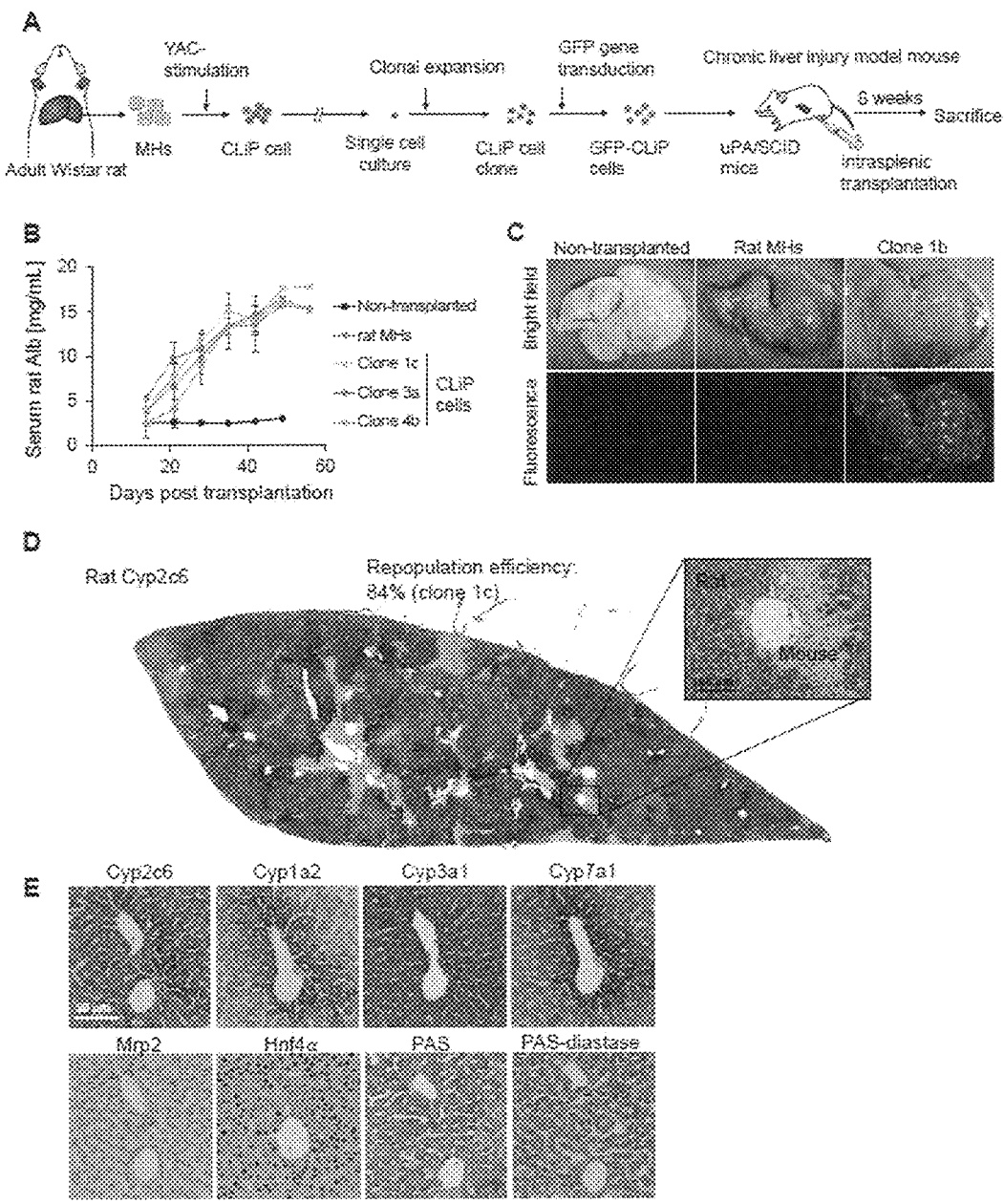
FIG. 8 Views showing liver regenerating effect in a mouse model with liver damage that has been transplanted with hepatic stem/progenitor cells derived from rat mature hepatocytes.

MH-LSC were transplanted into immunodeficient mice suffering from chronic liver damage to examine their regeneration ability. Urokinase-type plasminogen activator (uPA) transgenic mice (uPA/SCID mouse) crossbred with SCID mice were used. For a transplantation assay, three independent clones were selected and transduced with copGFP gene using lentivirus. Transduced cells were selected with puromycin and these labelled MH-LSC clones were transplanted into the spleens of the uPA/SCID mice at $1.5 \times 10^6$ cells/mouse (FIG. 8A). As a positive control, rat mature hepatocytes were transplanted at $2 \times 10^5$ cells/mouse. The rat serum ALB levels were monitored every 2 weeks following transplantation, which steadily increased for 8 weeks following transplantation when rat mature hepatocytes were transplanted (FIG. 8B). While no tumorigenesis was observed and many brown regions were contained in the entire image of the liver excised from the mouse transplanted with MH-LSC, the liver of the non-transplanted mouse was white presenting severe chronic liver damage (FIG. 8C, upper panel). From the entire image of fluorescent staining, the brown regions were confirmed to be composed of GFP-positive cells (FIG. 8C, lower panel), showing that MH-LSC ubiquitously replaced the injured liver. Moreover, the results from immunohistochemistry analysis of rat Cyp2c6 revealed that 84% of the entire liver of the MH-LSC-transplanted mouse was replaced with MH-LSC-derived cells (FIG. 8D). The immunohistochemistry analysis and PAS staining showed that the MH-LSC-derived cells evenly expressed various mature hepatocyte markers (Cyp2c6, Cyp1a2, Cyp3a1, Cyp7a1, Mrp2 and Hnf4a) and accumulated glycogen (FIG. 8E). Furthermore, MH-LSC-derived cells were also shown to be binuclear in high frequency. These results show that MH-LSC are capable of efficiently regenerating the injured liver and differentiating into functional hepatocytes without tumorigenesis.

Example 7: Expressions of Other Known LSC Markers for MH-LSC

The present inventors also performed quantitative RT-PCR for other reported hepatic progenitor cell markers such as delta homolog 1 (DLK1), leucine-rich repeat-containing G protein-coupled receptor 5 (LGRS) (Huch, M. et al., Nature, 494: 247-250 (2013); (Huch, M. et al., Cell, 160: 299-312 (2015)) and FoxL1 (Sackett, S. D. et al., Hepatology, 49: 920-929 (2009)), but their expression was neither detected in the presence nor in the absence of YAC. These results suggest that the YAC-induced proliferating cells partially mimic the gene expression profile but are not exactly the same as the previously reported hepatic progenitor cells.

Example 8: Induction of MH-LSC from Cryopreserved Mature Hepatocytes

Figure 9:
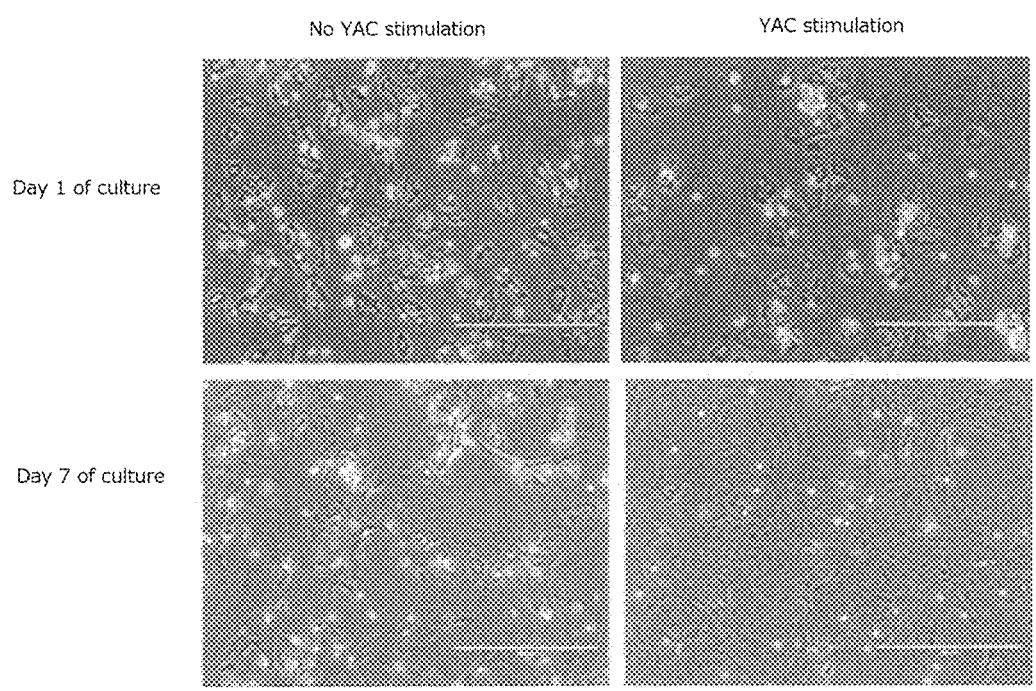
FIG. 9 Views showing induction of hepatic stem/progenitor cells from cryopreserved rat mature hepatocytes by YAC stimulation.

The present inventors examined whether LSC can be induced from cryopreserved rat hepatocytes by YAC stimulation. The cryopreserved rat hepatocytes were confirmed to result proliferation of cells with higher nuclear cytoplasmic (N/C) ratio than mature hepatocytes by YAC stimulation (FIG. 9). On the contrary, proliferating cells hardly emerged under no YAC stimulation and more cells resulted in apoptosis (FIG. 9).

Example 9: Induction of MH-LSC from Cryopreserved Human Hepatocytes

Figure 10:
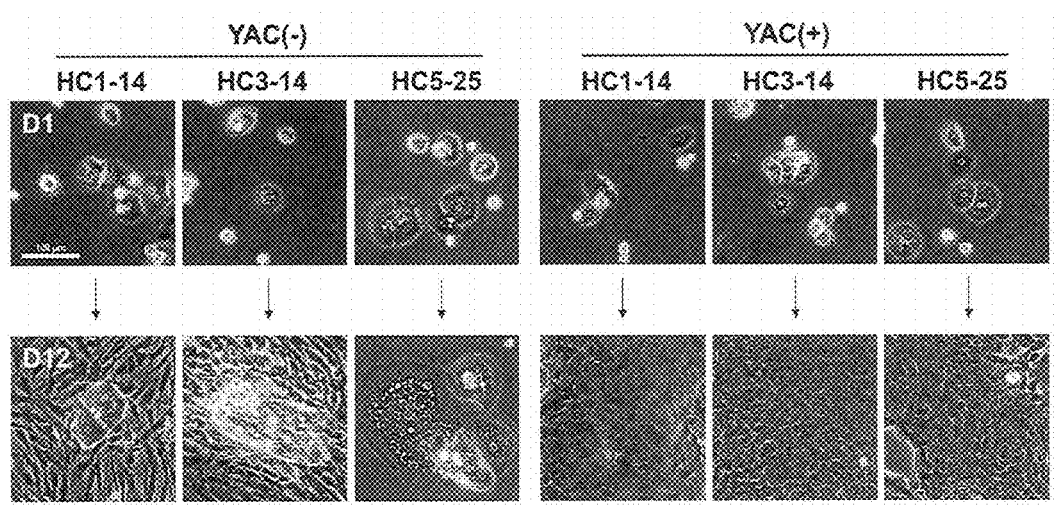
FIG. 10 Views showing induction of hepatic stem/progenitor cells from cryopreserved human hepatocytes by YAC stimulation.

The present inventors examined whether LSC can be induced from cryopreserved human hepatocytes by YAC stimulation. The cryopreserved human hepatocytes proliferated by YAC stimulation. Moreover, a colony having a form similar to that observed with rat hepatocytes emerged by YAC stimulation (FIG. 10).

Example 10: Passage of MH-LS Induced from Cryopreserved Human Hepatocytes

Figure 11:
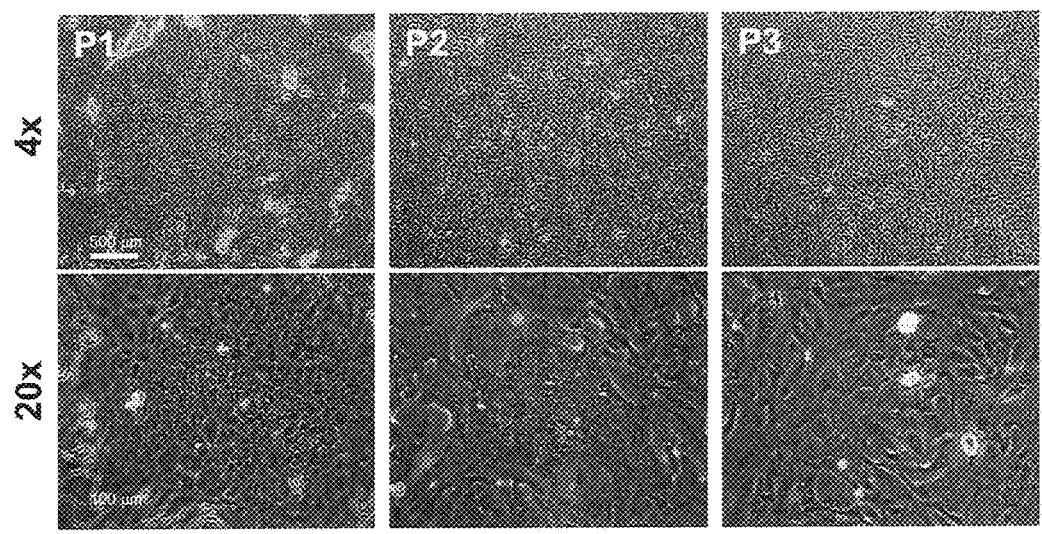
FIG. 11 Views showing results of passaging the hepatic stem/progenitor cells derived from cryopreserved human hepatocytes.

The present inventors conducted passage of MH-LS induced from cryopreserved human hepatocytes to examine whether serial passage was possible. As a result, MH-LS induced from cryopreserved human hepatocytes retained the proliferation ability after the third passage (FIG. 11).

INDUSTRIAL APPLICABILITY

Since hepatic stem/progenitor cells having self-regeneration ability and differentiation potency (bipotency) into hepatocytes and biliary epithelial cells can safely and rapidly be induced from hepatocytes without genetic modification according to the present invention, they are highly useful in possible applications to a drug-assessing system and liver regenerative medicine.

The present application is based on Patent Application No. 2016-003088 filed in Japan (filing date: Jan. 8, 2016), the contents of which are incorporated herein in their entirety.

The invention claimed is:

1. A method for producing hepatic stem/progenitor cells from mature mammalian hepatocytes, comprising contacting the mature mammalian hepatocytes with (i) a TGFβ-receptor inhibitor and a GSK3 inhibitor in vitro, (ii) a TGFβ-receptor inhibitor and a ROCK inhibitor in vitro, or (iii) a TGFβ-receptor inhibitor, a GSK3 inhibitor, and a ROCK inhibitor in vitro; thereby producing hepatic stem/progenitor cells;

wherein the hepatic stem/progenitor cells:
 (a) have self-regeneration ability;
 (b) are capable of differentiating into both hepatocytes and biliary epithelial cells; and
 (c) express EpCAM but not Dlk1 as a surface antigen marker;

wherein the concentration of the TGFβ-receptor inhibitor is in a range of 0.1-1 µM, the concentration of the GSK3 inhibitor is in a range of 1-10 µM, and the concentration of the ROCK inhibitor is in a range of 1-50 µM; and wherein the method is conducted without genetic modification of the cells.

2. The method according to claim 1, wherein contact between the hepatocytes and the TGFβ-receptor inhibitor is carried out by culturing the hepatocytes in the presence of the inhibitor.

3. The method according to claim 1, wherein the mammal is a human, a rat or a mouse.

* * * * *